US011077006B2

(12) United States Patent
Labedz et al.

(10) Patent No.: US 11,077,006 B2
(45) **Date of Patent: *Aug. 3, 2021**

(54) MEDICAL TABLE WITH LEG SUPPORT

(71) Applicant: American Sterilizer Company, Mentor, OH (US)

(72) Inventors: Christopher D. Labedz, Streetsboro, OH (US); Lance Clark Bellows, Painesville, OH (US); Yury Keselman, Beachwood, OH (US); Jeff M. Kalman, Cleveland Heights, OH (US); Paul D. Stephens, Twinsburg, OH (US)

(73) Assignee: American Sterilizer Company, Mentor, OH (US)

( * ) Notice: Subject to any disclaimer, the term of this patent is extended or adjusted under 35 U.S.C. 154(b) by 226 days.

This patent is subject to a terminal disclaimer.

(21) Appl. No.: 16/223,968

(22) Filed: Dec. 18, 2018

(65) Prior Publication Data

US 2019/0117489 A1 Apr. 25, 2019

Related U.S. Application Data

(63) Continuation of application No. 13/749,055, filed on Jan. 24, 2013, now Pat. No. 10,206,842.

(Continued)

(51) Int. Cl.

*A61F 5/048* (2006.01)
*A61F 5/042* (2006.01)

(Continued)

(52) U.S. Cl.

CPC ....... *A61G 13/123* (2013.01); *A61G 13/0036* (2013.01); *A61G 13/0063* (2016.11);

(Continued)

(58) Field of Classification Search

CPC .............. A61G 13/123; A61G 13/0036; A61G 13/0063; A61G 13/0081; A61G 13/125;

(Continued)

(56) References Cited

U.S. PATENT DOCUMENTS

| | | | |
|---|---|---|---|
| 824,612 | A | 6/1906 | Bartlett |
| 3,745,996 | A | 7/1973 | Rush, Sr. |

(Continued)

FOREIGN PATENT DOCUMENTS

WO WO 2006/028788 A2 3/2006

OTHER PUBLICATIONS

International Search Report from corresponding International Patent Application No. PCT/US2013/023178, dated Mar. 22, 2013.

(Continued)

*Primary Examiner* — Ophelia A Hawthorne
*Assistant Examiner* — Camtu T Nguyen
(74) *Attorney, Agent, or Firm* — Kusner & Jaffe

(57) ABSTRACT

A patient support apparatus is defined that includes a patient support having one or more pads for supporting a patient's torso and hip in a generally horizontal orientation. At least one, elongated leg support extends from the patient support. The leg support is movable through a generally horizontal plane. A portion of the leg support is declinable and inclinable from the horizontal plane. A traction device is connected to the leg support. The traction device is attachable to a patient's leg and operable to exert a traction force on the patient's leg along an axis of the traction device. The traction device is connected to the leg support by a slide assembly and the traction device can be secured stationary relative to the leg support or the traction device can slide relative to the leg support.

26 Claims, 16 Drawing Sheets

Related U.S. Application Data

(60) Provisional application No. 61/590,943, filed on Jan. 26, 2012.

(51) Int. Cl.
*A61F 5/045* (2006.01)
*A61G 13/12* (2006.01)
*A61G 13/00* (2006.01)

(52) U.S. Cl.
CPC ........ *A61G 13/0081* (2016.11); *A61G 13/125* (2013.01); *A61G 13/1245* (2013.01)

(58) Field of Classification Search
CPC .. A61G 13/1245; A61G 7/0755; A61G 7/075; A61G 13/08; A61F 5/04; A61F 5/042; A61F 5/048; A61F 5/3769; A61F 5/37; A61F 5/40; A61F 5/00; A61F 5/045; A61H 2001/0248; A61H 2001/0259; A61H 1/0222; A61H 1/0218; A61H 1/0237; A61H 1/0266; A61H 1/024; A61H 1/02; A61H 1/00
See application file for complete search history.

(56) References Cited

U.S. PATENT DOCUMENTS

| | | | | |
|---|---|---|---|---|
| 3,766,384 | A | 10/1973 | Anderson | |
| 4,624,245 | A | 11/1986 | Mullin et al. | |
| 4,872,656 | A * | 10/1989 | Brendgord ......... | A61G 13/0036 5/601 |
| 5,025,802 | A | 6/1991 | Laico et al. | |
| 5,290,222 | A | 1/1994 | Feng et al. | |
| 5,645,079 | A | 7/1997 | Zahiri et al. | |
| 5,658,315 | A | 8/1997 | Lamb et al. | |
| 5,802,641 | A | 9/1998 | Van Steenburg | |
| 6,446,287 | B2 | 9/2002 | Borders | |
| 6,634,043 | B2 | 10/2003 | Lamb et al. | |
| 6,640,363 | B1 | 11/2003 | Pattee et al. | |
| 6,663,055 | B2 | 12/2003 | Boucher et al. | |
| 6,854,145 | B2 | 2/2005 | Ruehl et al. | |
| 6,895,969 | B2 | 5/2005 | Malcolm et al. | |
| 7,246,390 | B2 | 7/2007 | Mitsuishi et al. | |
| 7,739,762 | B2 | 6/2010 | Lamb et al. | |
| 7,762,975 | B2 | 7/2010 | Memminger | |
| 7,947,006 | B2 | 5/2011 | Torrie et al. | |
| 8,001,633 | B2 | 8/2011 | Swain, Jr. | |
| 2002/0023298 | A1 | 2/2002 | Lamb et al. | |
| 2004/0133983 | A1 | 7/2004 | Newkirk et al. | |
| 2006/0185091 | A1 | 8/2006 | Jackson | |
| 2007/0161935 | A1 | 7/2007 | Torrie et al. | |
| 2007/0251011 | A1 | 11/2007 | Matta et al. | |
| 2007/0265635 | A1 | 11/2007 | Torrie et al. | |
| 2010/0023016 | A1 | 1/2010 | Botimer | |
| 2010/0263129 | A1 | 10/2010 | Aboujaoude | |
| 2011/0023893 | A1 | 2/2011 | Striggow et al. | |
| 2011/0190676 | A1 | 8/2011 | Torrie et al. | |

OTHER PUBLICATIONS

Non-final Office Action issued in corresponding U.S. Appl. No. 13/749,055 dated Mar. 26, 2015.
Final Office Action issued in corresponding U.S. Appl. No. 13/749,055 dated Nov. 3, 2015.
Non-final Office Action issued in corresponding U.S. Appl. No. 13/749,055 dated Sep. 6, 2016.
Final Office Action issued in correspondiug U.S. Appl. No. 13/749,055 dated Mar. 31, 2017.
Non-final Office Action issued in corresponding U.S. Appl. No. 13/749,055 dated Sep. 7, 2017.
Final Office Action issued in corresponding U.S. Appl. No. 13/749,055 dated May 2, 2018.

* cited by examiner

MEDICAL TABLE WITH LEG SUPPORT

RELATED APPLICATIONS

The present application is a continuation of U.S. application Ser. No. 13/749,055, filed Jan. 24, 2013, which claims the benefit of U.S. Provisional Application Ser. No. 61/590,943, filed Jan. 26, 2012, said patent applications being fully incorporated herein by reference.

FIELD OF THE INVENTION

The present invention relates generally to support structures for supporting patients during surgical procedures, and more particularly, to orthopedic tables for supporting a patient during surgical procedures, such as a knee replacement or a hip replacement.

BACKGROUND OF THE INVENTION

Certain surgical procedures, such as knee replacements or hip replacements, require manipulation and re-orientation of a patient's leg from its normal position during a surgical procedure. For example, during a total hip arthroplasty ("THA") or replacement surgery, the femoral head of the femur bone is separated from the hip socket or acetabulum, and the femoral head is then removed from the femur. To facilitate this procedure and the insertion of replacement parts, it is necessary to re-orientate the patient's leg so as to position and orient the femur in a position most convenient for the surgeon and surgical team.

The present invention provides an orthopedic table for more rapidly positioning and orienting a patient's leg, most specifically, the patient's femur, during a total hip arthroplasty ("THA").

SUMMARY OF THE INVENTION

In accordance with a preferred embodiment of the present invention, there is provided a patient support apparatus, comprising a patient support having one or more pads for supporting a patient's torso and hip in a generally horizontal orientation. At least one, elongated leg support extends from the patient support. The leg support is movable through a generally horizontal plane. A portion of the leg support is declinable and inclinable from the horizontal plane. A traction device is connected to the leg support. The traction device is attachable to a patient's leg and operable to exert a traction force on the patient's leg along an axis generally parallel to the leg support. The traction device is connected to the leg support by a slide assembly and the traction device can be secured stationary relative to the leg support or the traction device can slide relative to the leg support.

In accordance with another aspect of the present invention, there is provided a leg support for an orthopedic table. The leg support includes a proximal leg support section attachable to an orthopedic table to be reciprocally movable in a generally horizontal plane about a first vertical axis. An elongated spar section is connected to the proximal leg support section. The elongated spar section is reciprocally movable in a horizontal plane about a second vertical axis generally parallel to the first vertical axis, and is further movable downward and upward relative to the horizontal plane. A traction device is mounted to the elongated spar section. The traction device has a foot support attachable to a patient's foot. The traction device extends along an axis and operable to reciprocally move the foot support along the axis. The traction device is reciprocally movable in a linear direction along the axis relative to the spar section, and is rotatable about an axis generally perpendicular to the axis of the traction device.

In accordance with another aspect of the present invention, there is provided an orthopedic table, comprising a patient support for supporting the head and torso of a patient and a leg support having an elongated spar section. The spar section is movable about a generally vertical axis and about a generally horizontal axis. A mounting assembly is provided for mounting a traction device to the spar section. The traction device is attachable to the mounting assembly. The traction device has a foot support for attachment to a patient's foot, wherein the foot support is movable along an axis extending through the traction device and is rotatable about the axis. The traction device is rotatable about an axis through the mounting assembly, lockable in a fixed position relative to the mounting assembly and the spar, and unlockable from a fixed position so as to be reciprocally movable relative to the mounting assembly along the axis of the traction device. The traction device is able to follow movement of a patient's foot during movement of the spar when the traction device is unlocked from a fixed position relative to the mounting assembly.

In accordance with yet another aspect of the present invention, there is provided a patient support apparatus, comprising a patient support that has one or more pads for supporting a patient's torso and hip in a generally horizontal orientation. At least one, elongated leg support extends from the patient support. The leg support is movable through a generally horizontal plane, and a portion of the leg support is declinable from the horizontal plane. A traction device is connected to the portion of the leg support. The traction device is attachable to a patient's leg and is operable to exert a traction force on the patient's leg along an axis generally parallel to the portion of the leg support. The traction device is connected to the leg support by a slide assembly, wherein the traction device can be secured stationary relative to the leg support, or the traction device can slide relative to the leg support.

An advantage of the present invention is an orthopedic table for supporting a patient during a surgical procedure, such as a knee replacement or a hip replacement.

Another advantage of the present invention is an orthopedic table as described above having at least one leg support for supporting and positioning a patient's leg during a surgical procedure.

Another advantage of the present invention is an orthopedic table as described above wherein the leg support is movable and positionable through a horizontal plane.

Another advantage of the present invention is an orthopedic table as described above wherein a portion of said leg portion is declinable and inclinable from said horizontal plane.

Another advantage of the present invention is an orthopedic table as described above having a traction device mounted to the leg support for attachment to a patient's leg for manipulating and adjusting a patient's leg during a surgical procedure.

A further advantage of the present invention is an orthopedic table as described above, wherein the traction device is operable to move a patient's leg axially along an axis generally parallel to the lengthwise direction of a patient's leg.

A still further advantage of the present invention is an orthopedic table as described above, wherein the traction device has a course-adjustment feature allowing free movement of the traction device relative to the leg support during movement of the leg support.

A still further advantage of the present invention is an orthopedic table as described above, wherein the traction device has a fine-adjustment feature allowing small adjustment to the traction device to facilitate fine, precise lengthwise adjustment of a patient's leg.

A still further advantage of the present invention is an orthopedic table as described above, wherein the traction device has means for facilitating angular rotation of a patient's leg relative to the general axis of the patient's leg.

A still further advantage of the present invention is an orthopedic table as described above, wherein the traction device can simultaneously produce axial movement and angular rotation of a patient's leg.

A still further advantage of the present invention is an orthopedic table as described above, wherein axial movement and angular rotation of a patient's leg can be produced using only one hand of a member of a surgical team.

A still further advantage of the present invention is an orthopedic table as described above, wherein axial and angular manipulation of a patient's leg and declination of a portion of the leg support can be performed simultaneously by a single member of a surgical team.

Another advantage of the present invention is an orthopedic table as described above, wherein said traction device has a course-adjustment feature and a fine-adjustment feature, wherein the course-adjustment feature is removable from the traction device.

Another advantage of the present invention is an orthopedic table as described above having a patient support surface for supporting the head and torso of a patient.

A still further advantage of the present invention is an orthopedic table as described above having a post positioned on a patient support surface, the post to be disposed between a patient's legs to prevent movement of the patient toward the traction device when tension is applied to the patient's leg by the traction device.

A still further advantage of the present invention is an orthopedic table as described above having a patient support with a post movable between at least two positions to accommodate patients of different height and length.

Another advantage of the present invention is an orthopedic table as described above having a femur support for supporting a patient's femur during a total hip arthroplasty ("THA") or replacement surgery.

Another advantage of the present invention is an orthopedic table as described above having a femur support, wherein the femur support is vertically adjustable.

A still further advantage of the present invention is an orthopedic table as described above, wherein the femur support has a structure that allows gross, i.e., large, vertical adjustment of the femur support.

Another advantage of the present invention is an orthopedic table as described above, wherein the femur support has a structure that allows fine, i.e., small, precise, vertical adjustments of the femur support.

A still further advantage of the present invention is an orthopedic table as described above having a femur support that includes a femur hook insertable into a patient's leg through an incision into the patient's leg to capture and support the femur.

A still further advantage of the present invention is an orthopedic table as described above, wherein said femur support includes an elongated support bracket wherein said femur support hook is positionable at different locations along the elongated support bracket.

A still further advantage of the present invention is an orthopedic table as described above wherein the femur hook is positionable at different orientations relative to said support bracket at each of the different locations along the elongated support bracket.

A still further advantage of the present invention is an orthopedic table as described above wherein the femur hook is removable from the elongated support bracket.

A further advantage of the present invention is an orthopedic table as described above wherein the femur support assembly is removable from the orthopedic table and mountable to either side of the patient's support surface.

These and other advantages will become apparent from the following description of a preferred embodiment taken together with the accompanying drawings and the appended claims.

BRIEF DESCRIPTION OF THE DRAWINGS

The invention may take physical form in certain parts and arrangement of parts, a preferred embodiment of which will be described in detail in the specification and illustrated in the accompanying drawings which form a part hereof, and wherein.

DETAILED DESCRIPTION OF PREFERRED EMBODIMENT

Figure 1:
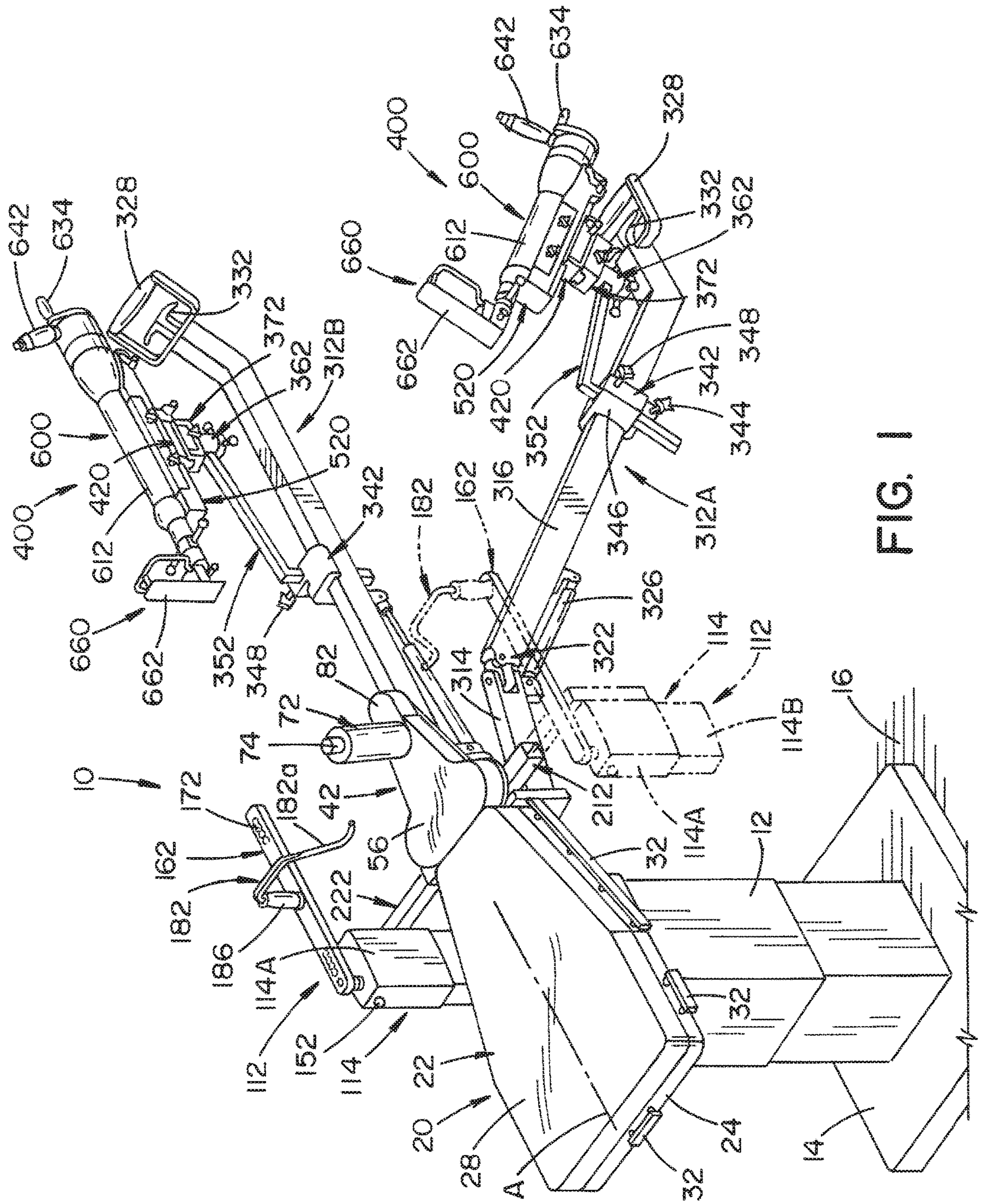
FIG. 1 is a perspective view of an orthopedic table, illustrating a preferred embodiment of the present invention.

Referring now to the drawings wherein the showings are for the purpose of illustrating a preferred embodiment of the invention only and not for the purpose of limiting same, FIG. 1 shows an orthopedic table 10 illustrating a preferred embodiment of the present invention. Broadly stated, orthopedic table 10 is comprised of a patient support 20 that is mounted to a support column 12 that extends upward from a base 14. The patient support 20 is symmetrical about a central axis, designated "A" in the drawings, that extends along the length of the patient support 20. The support column 12 and base 14 are conventionally known and, therefore, are not shown and shall not be described in great detail. The support column 12 is typically a telescoping structure that allows for vertical adjustment of the patient support 20. The base 14 may be motorized so as to allow movement of the orthopedic table 10 along the floor 16 or may be fixedly secured to the floor 16 in a stationary position.

In the embodiment shown, the patient support 20 is comprised of a head/torso support 22 and a sacral support 42. The head/torso support 22 is generally comprised of a support frame 24 having a generally planar upper surface. A resilient pad or mattress 28 is disposed and/or secured to the support frame 24. In the embodiment shown, the support frame 24 is an integrally formed member. In the embodiment shown, side rails 32 are attached to the lateral sides of support frame 24. Support frame 24 and pad/mattress 28 thereon provide support for a patient's head and torso.

Figure 4:
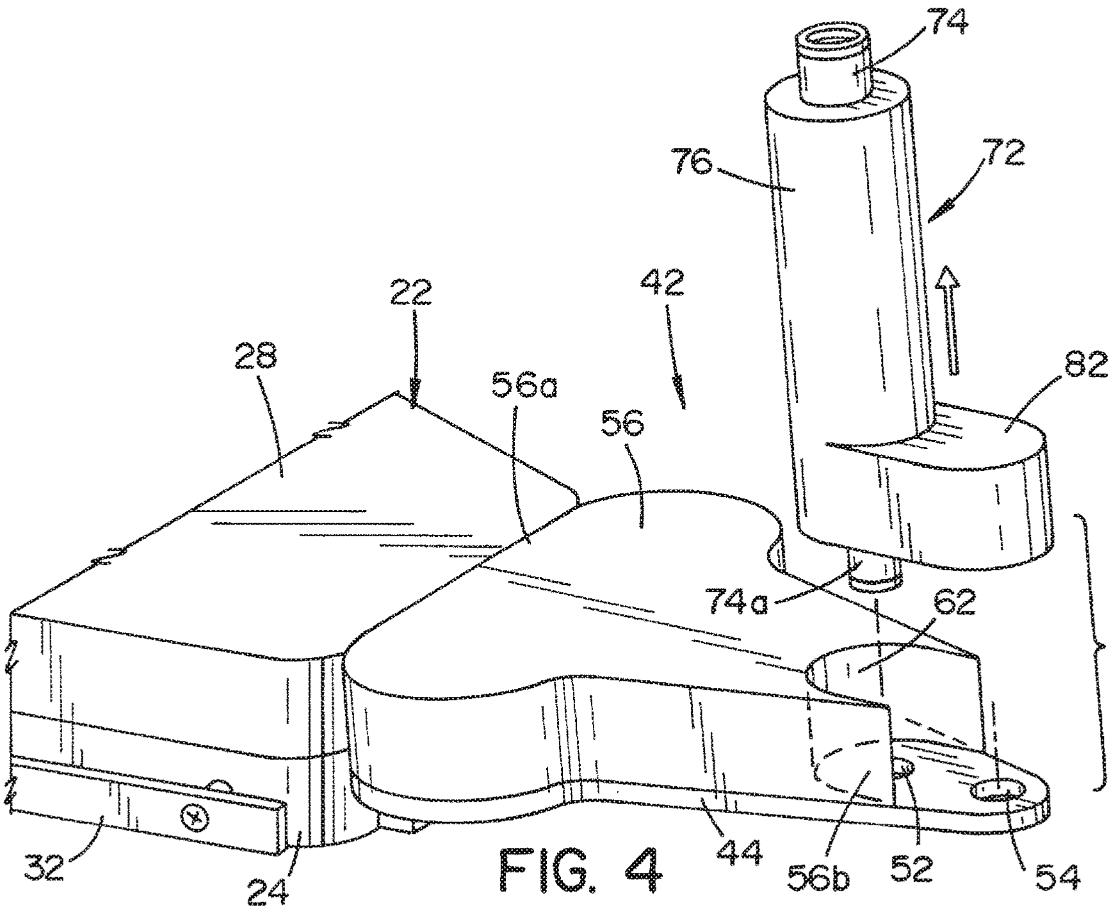
FIG. 4 is a perspective, exploded view of the sacral pad assembly shown in FIG. 3, showing the post pad separated from the sacral pad.
Figure 6:
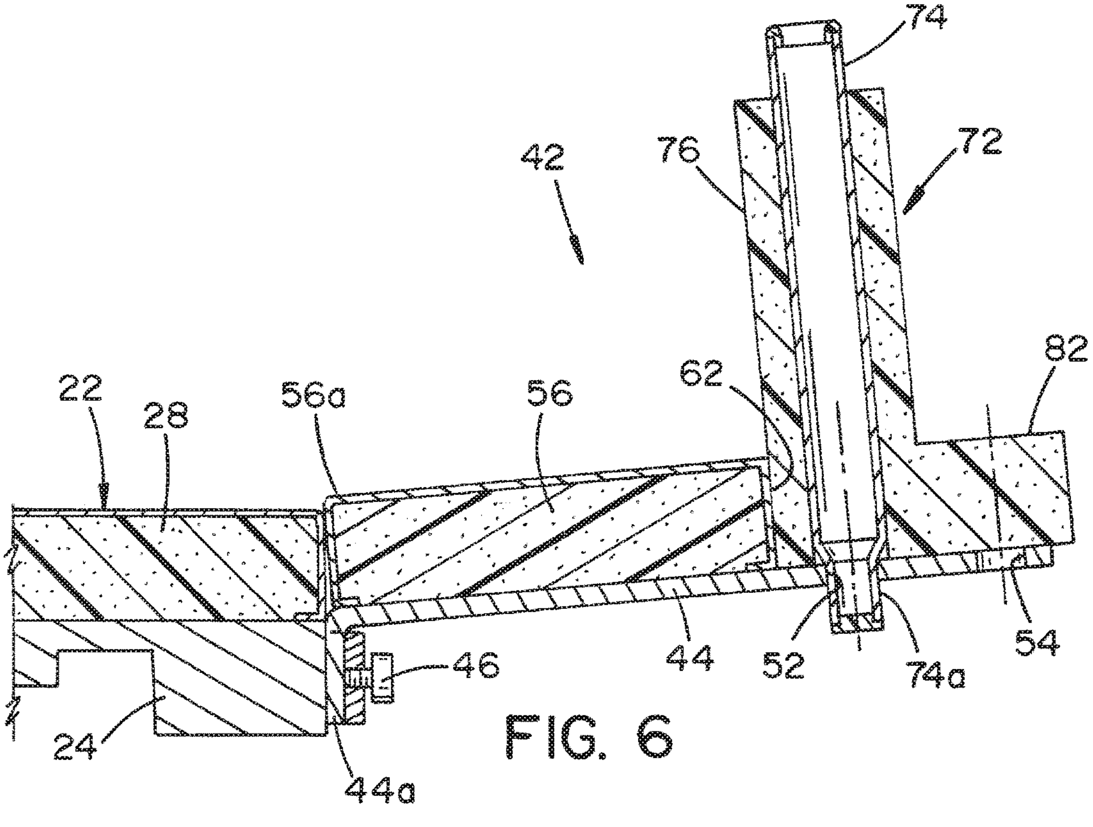
FIG. 6 is a sectional view taken along lines 6-6 of FIG. 3.

The sacral support 42 is positioned at one end of the torso and head/torso support 22. Sacral support 42 is comprised of a generally triangular, sacral plate 44 having a downward extending flange 44*a* formed at a first end thereof. Sacral plate 44 is symmetrical about axis A of patient support 20 and is attachable to support frame 24 of the head/torso support 22. Conventional fasteners 46 extending through holes in bracket 34 capture flange 44*a* against support frame 24, as best seen in FIG. 6. Two spaced-apart openings 52, 54, best seen in FIG. 4, are formed through the sacral plate 44 adjacent the free end thereof. Openings 52, 54 are aligned along axis A of patient support 20. A resilient sacral pad or mattress 56 is disposed on and connected to the sacral plate 44. Sacral pad 56 has a first end 56*a* that abuts the head/torso support 22, and the second end 56*b* is formed to have a cylindrical notch 62 or recess formed therein. As illustrated in the drawings, sacral pad 56 is shorter in length than sacral plate 44. A positioning post 72 is provided to be positioned on the free end of sacral plate 44. Positioning post 72 is basically comprised of a rigid, structural pin 74 having a resilient, cylindrical pad 76 surrounding a major portion of the pin. Pin 74 has a lower, end portion 74*a* of reduced dimension that extends from pad 76. The lower, end portion 74*a* of pin 74 is dimensioned to be received within openings 52, 54 formed at the end of sacral plate 44. In a preferred embodiment, pin 74 is formed of a carbon fiber composite. In the embodiment shown, pin 74 is cylindrical in shape and a tubular cylindrical pad 76 surrounds pin 74. A base pad portion 82 is formed near the lower end of cylindrical pad 76 and extends to one side thereof. When viewed from above along the axis of pin 74, base pad portion 82 has an obround shape, wherein base pad portion 82 has parallel sides and rounded, cylindrical ends. Base pad portion 82 of positioning post 72 has a thickness corresponding to the thickness of sacral pad 56. The rounded, cylindrical ends of base pad portion 82 are dimensioned to mate with the cylindrical recess 62 formed in sacral pad 56.

As shown in the drawings, lower end 74*a* of pin 74 extends from the padded portions of resilient pad 76 and base portion 82 such that lower end portion 74*a* of pin 74 may be positioned within openings 52, 54 formed in sacral plate 44. In this respect, openings 52, 54 in sacral plate 44 are disposed such that positioning post 72 may be mounted to sacral plate 44 in one of two positions, as illustrated in the drawings. In one position (shown in FIG. 3), positioning post 72 is disposed closer to head/torso support 22. In a second position (best seen in FIG. 5), cylindrical pad 76 of positioning post 72 is disposed in opening 54 and are therefore located further from the end of head/torso support 22. In both positions, the rounded, cylindrical ends of base pad portion 82 of positioning post 72 mate closely with cylindrical notch or recess 62 formed in the free, second end of sacral pad 56.

As shall be described in greater detail below, pin 74 and pad 76 of positioning post 72 is provided to be positioned between the legs of a patient to position the patient on the patient support 20. The dual hole configuration in sacral plate 44 allows for adjustment of the position of pin 74 and pad 76 in relation to the size of a patient, as shall be described below.

Figure 7:
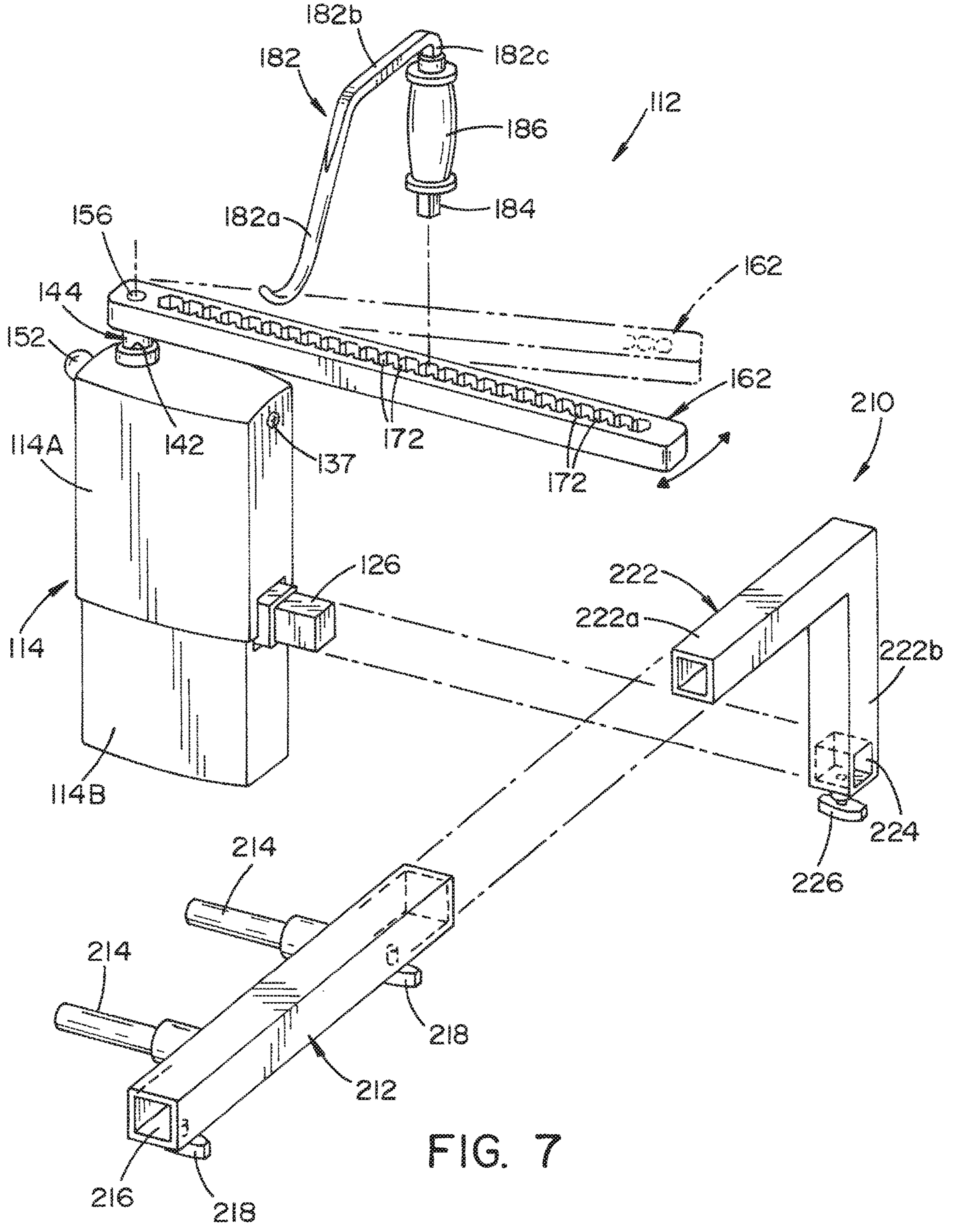
FIG. 7 is an exploded, perspective view of a femur support/lift assembly and an adjustable mounting assembly for mounting the support/lift assembly to the orthopedic table.
Figure 8:
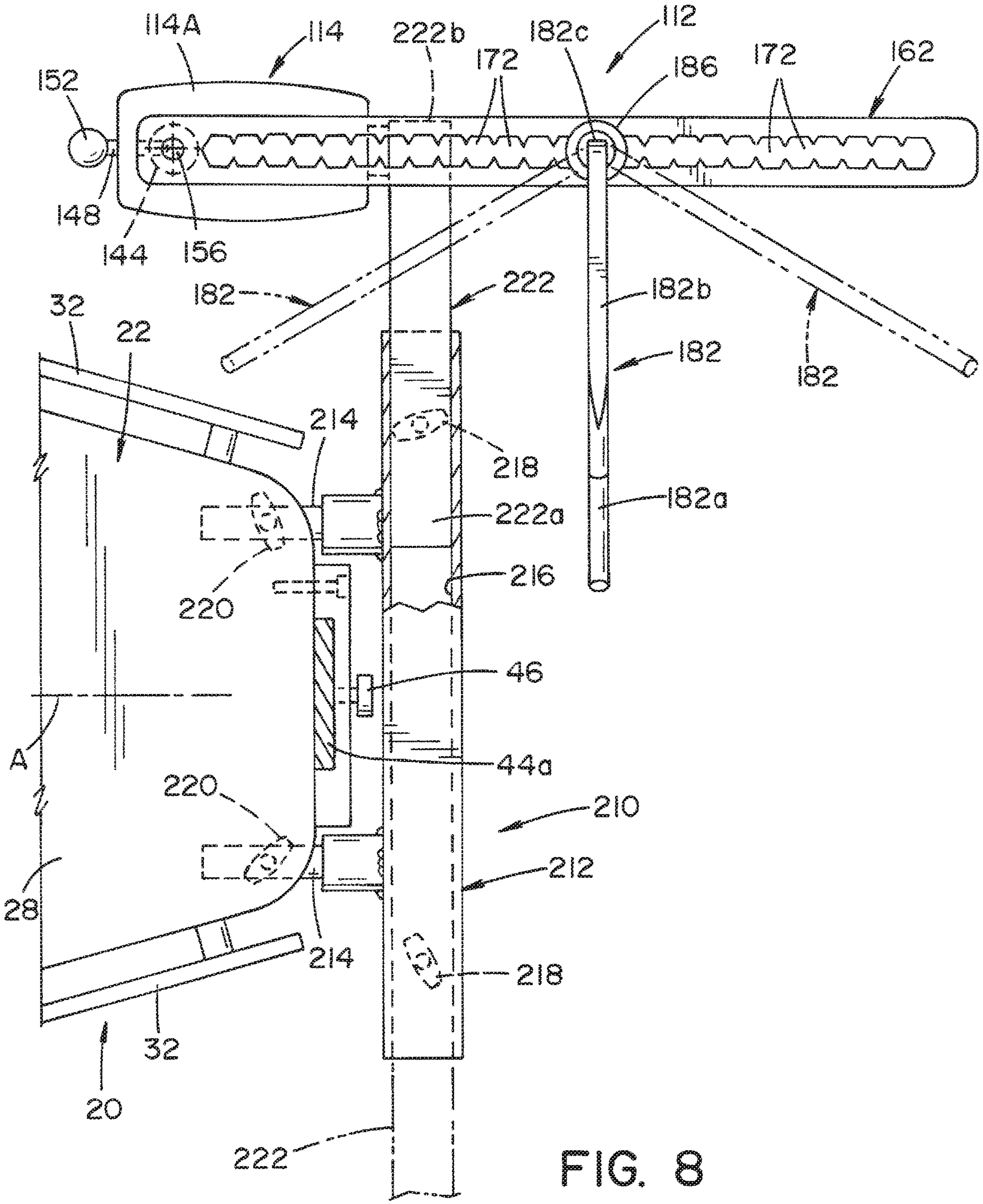
FIG. 8 is a partially sectioned, top plan view showing the adjustable mounting assembly attached to the orthopedic table and the femur support/lift assembly attached to the mounting assembly to one side of the orthopedic table, and further showing a femur support hook positioned in one of a plurality of aligned femur-support-hook mounting openings in a support bracket, illustrating in phantom how the femur support hook may be positioned in different orientations in each of the femur-hook-mounting openings.
Figure 9:
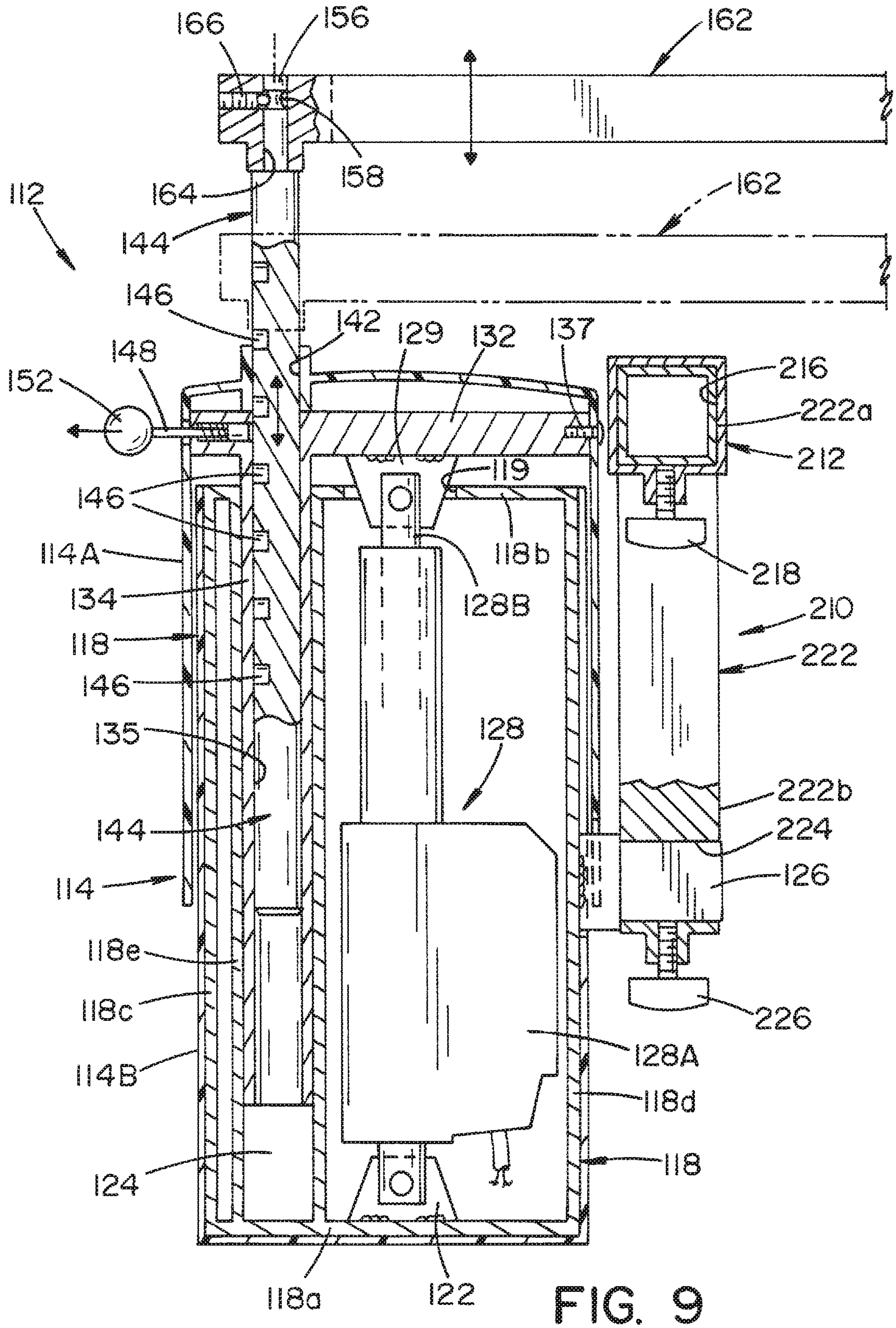
FIG. 9 is a cross-sectional view of the femur support/lift assembly and adjustable mounting assembly, showing the femur support/lift assembly mounted to the adjustable mounting assembly, and illustrating how the position of a femur hook support may be vertically adjusted in relatively large amounts using a gross adjustment feature.
Figure 10:
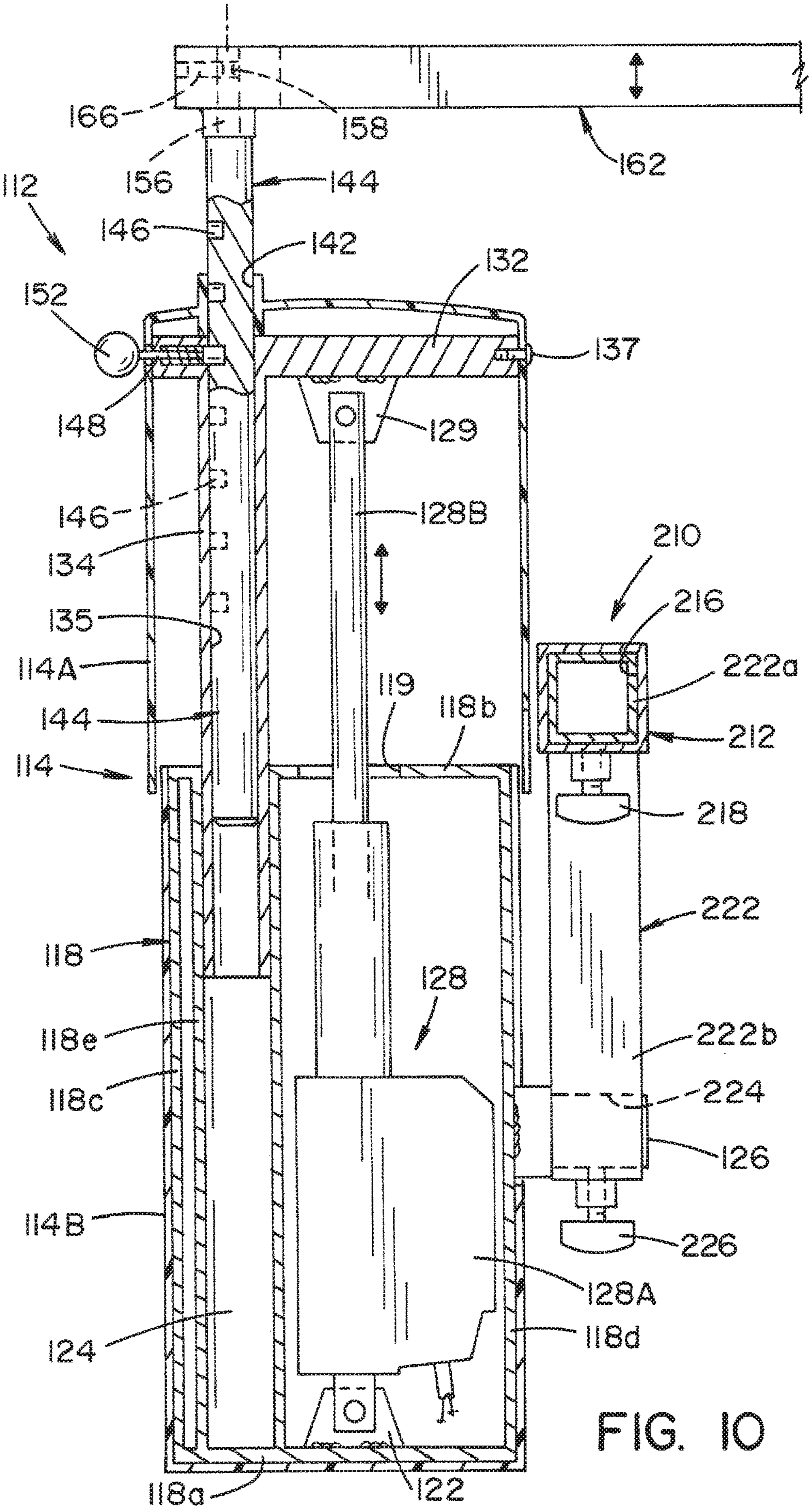
FIG. 10 is a cross-sectional view of the femur support/lift assembly and adjustable mounting assembly, showing the femur support/lift assembly mounted to the adjustable mounting assembly, and illustrating how the position of a femur hook support bracket may be vertically adjusted in relatively fine adjustments using a fine adjustment feature.

Referring now to FIGS. 7-10, a femur support assembly 112 is best seen. The femur support assembly 112 includes a housing 114. Housing 114 includes an upper housing section 114A and a lower housing section 114B. Upper housing section 114A is dimensioned to telescope over the lower housing section 114B, as shall be described in greater detail below. A support/guide structure 118, best seen in FIGS. 9 and 10, is disposed within lower housing section 114B. Support/guide structure 118 includes a bottom wall 118*a*, a top wall 118*b*, and two spaced-apart side walls 118*c*, 118*d*, that extend upward from bottom wall 118*a*. A mounting bracket 122 extends upward from bottom wall 118*a*. To one side of the bracket, a tubular post 118*e* extends vertically upward from bottom wall 118*a* to top wall 118*b* of housing 118. In the embodiment shown, tubular post 118*e* is cylindrical in shape.

A block 126, extends from side wall 118*d* of the support-guide structure in the lower housing section 114B through the lower housing section 114B. In the embodiment shown, block 126 has a rectangular cross section.

A powered lifting device 128 is disposed within support/guide structure 118 in lower housing section 114B. In the embodiment shown, lifting device 128 is a linear actuator having a body portion 128A and a movable rod portion 128B that extends from body portion 128A. Rod portion 128B is operable to move along a linear path relative to body portion 128A. The lower end lifting device 128 is pinned to bracket 122 that extends from bottom wall 118*a* of support/guide structure 118. The free end of rod portion 128A extends through an opening 119 in top wall 118*b* of support/guide structure 118 and is pinned to a bracket 129 that extends downward from a horizontal support plate 132. Support plate 132 includes an elongated sleeve 134 that extends vertically downward from support plate 132. Sleeve 134 extends generally parallel to rod portion 128B of lifting device 128. Sleeve 134 is dimensioned to be received within the cylindrical opening defined by tubular post 118*e* that forms part of support/guide structure 118 in lower housing section 114B. In this respect, in the embodiment shown, sleeve 134 is cylindrical in shape and defines an elongated, cylindrical opening 135 that extends through sleeve 134 and through support plate 132. In the embodiment shown, sleeve 134 is formed as an integral part of support plate 132. As will be described in greater detail below, tubular post 118*e* acts as a guide for sleeve 134.

The upper housing section 114A is dimensioned to be mounted to support plate 132 by conventional fasteners 137. An upper portion of sleeve 134 is in registry with an opening 142 through the upper portion of upper housing section 114, as best seen in FIGS. 9 and 10. Sleeve 134 on support plate 132 is dimensioned to receive an elongated rod 144 having a plurality of spaced-apart, aligned cylindrical bores 146 formed along one side thereof. Rod 144 is dimensioned to slide vertically within sleeve 134. In this respect, rod 144 is movable relative to support plate 132 and upper housing section 114A. A spring biased locking pin 148 having a knob 152 on one end thereof is dimensioned to be received in one of the plurality of cylindrical bores 146 formed in the side of elongated rod 144. As shown in FIGS. 9 and 10, spring-biased locking pin 148 extends through support plate 132 to lock rod 144 in one of several positions relative to support plate 132 and upper housing section 114A.

A mounting pin portion 156 of reduced diameter is formed at the upper end of rod 144 to define a support structure. An elongated hook support 162 is mounted to pin portion 156 on the upper, free end of rod 144. As best seen in FIG. 9, a cylindrical bore 164 is formed in one end of the elongated hook support 162. Cylindrical bore 164 is dimensioned to receive pin portion 156 on the upper end of rod 144. Pin portion 156 includes an annular groove 158 having a generally semi-circular cross-section. An oval point set screw 166, extending through the end of elongated hook support 162 communicates with annular groove 158 in pin portion 156 to lock hook support 162 onto rod 144 and to allow rotation of hook support 162 about rod 144 in a horizontal plane perpendicular to the axis of the vertically oriented rod 144, as illustrated by the arrow in FIG. 7.

Hook support 162 is an elongated structure having a plurality of overlapping apertures 172 formed along the length thereof. Each aperture 172 may be formed in the shape of a polygon or a star, or have a star-like configuration radiating from or disposed about a center. In the embodiment shown, each aperture 172 is in the shape of a hexagon. Each aperture 172 defines a mounting position for a femur hook 182.

The femur hook 182, best seen in FIG. 7, is generally comprised of an elongated bar that is bent to have a J-shaped hook portion 182*a* at one end, a horizontal, intermediate leg portion 182*b* and a generally vertical leg portion 182*c*. Vertical leg portion 182*c* of femur hook 182 has a post 184 formed at the lower end thereof. A handle 186 or grip is formed above post 184 to facilitate gripping and handling of femur hook 182. Post 184 on femur hook 182 is dimensioned to be received within apertures 172 formed in hook support 162. In the embodiment shown, post 184 is hexagonal in shape. As best illustrated in FIG. 8, because of the hexagonal shape of apertures 172 and the hexagonal shape of post 184 on femur hook 182, femur hook 182 may be positioned in one of six different positions within each hexagonal aperture 172 in hook support 162. Hook support 162 and femur hook 182 are preferably formed of metal, such as, by way of example and not limitation, stainless steel.

Referring now to FIG. 7, a mounting assembly 210 for mounting femur support assembly 112 to orthopedic table 10 is best seen. In the embodiment shown, mounting assembly 210 is basically comprised of a tubular cross member 212 and an L-shaped support 222. Cross member 212 has a pair of spaced-apart pins 214 extending from one side thereof. Tubular cross member 212 defines an inner opening 216 therethrough of generally uniform cross-sectional shape. Thumb screws 218 are located at each end of cross member 212 and extend into opening 216. Pins 214 are dimensioned to be received within sockets formed within the support frame 24 of orthopedic table 10. Thumb screws 220, best seen in phantom in FIG. 8, extending through threaded openings into the sockets are adapted to engage pins 214 on cross member 212 to lock cross member 212 in a horizontal position relative to support frame 24 of orthopedic table 10. Each end of cross member 212 is dimensioned to receive one leg 222*a* of L-shaped support member 222. In the embodiment shown, both the tubular cross member 212 and the L-shaped support 222 have rectangular cross-sections and are respectively dimensioned such that first leg 222*a* of L-shaped support 222 may be received within one end of inner opening 216 defined by tubular cross member 212 and move telescopically therein. The thumb screw 218 associated with the one end is used to secure L-shaped support 222 in cross member 212. L-shaped support 222 is disposed within tubular cross member 212 such that a second leg 222*b* of support 222 extends vertically downward relative to the patient support 20 surface of orthopedic table 10. The lower end of second leg 222*b* of L-shaped support 222 has a rectangular, transverse opening 224 extending therethrough. Opening 224 is dimensioned to receive the rectangular block 126 that extends from lower housing section 114B of the femur support assembly 112, as illustrated in FIG. 7. A thumb screw 226 that is aligned to extend axially along the length of second leg 222*b* of L-shaped support 222 secures the femur support assembly 112 by locking rectangular block 126 to second leg 222*b* of L-shaped support 222.

According to one aspect of the present invention, first leg portion 222*a* of L-shaped support 222 may be inserted into either end of tubular cross member 212. Moreover, rectangular block 126 on femur support assembly 112 may be inserted through either end of opening 224 through second leg portion 222*b* of L-shaped support 222. In this respect, femur support assembly 112 may be positioned and used on either side of orthopedic table 10, as shall be described in greater detail below.

Figure 2:
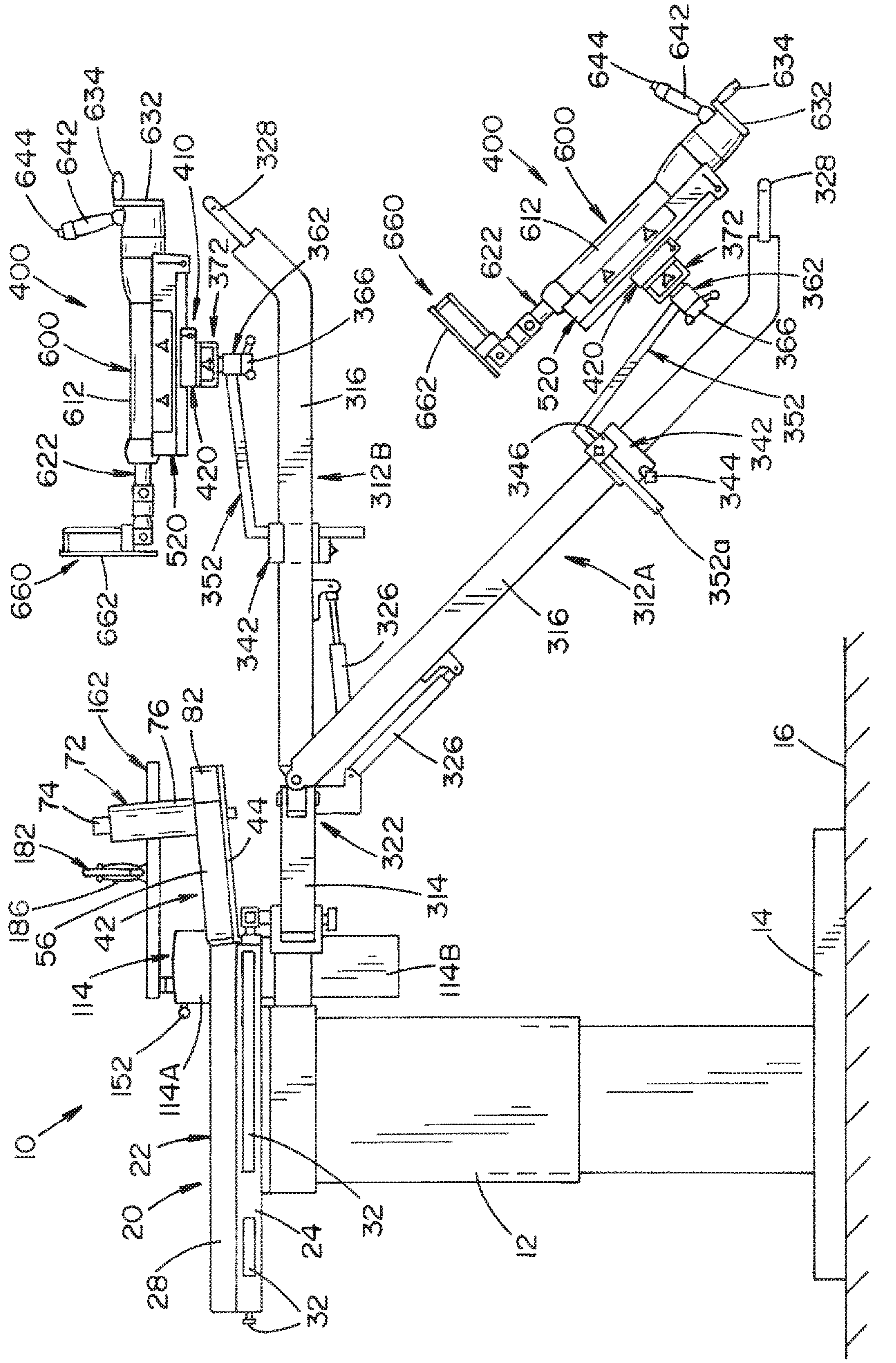
FIG. 2 is a side, elevational view of the orthopedic table shown in FIG. 1.

Referring now to FIGS. 1 and 2, two, side-by-side leg supports 312A, 312B extend from support frame 24 of orthopedic table 10. Leg support 312A is attached to support frame 24 below sacral support 42 and is pivotable about a generally vertical axis. In the embodiment shown, leg support 312A is comprised of a proximal section 314 and an elongated spar section 316. One end of the proximal section 314 is connected to table support frame 24 to be pivotable about the aforementioned vertical axis. The other end of proximal section 314 is connected to one end of elongated spar section 316 by a joint assembly 322. Joint assembly 322 allows the elongated spar section 316 to pivot about a vertical axis relative to the proximal section 314 and to be fixedly secured at select angular positions relative to the vertical axis. More specifically, joint assembly 322 allows elongated spar section 316 to pivot about a vertical axis that is generally parallel to the vertical axis connecting the first end of the proximal section 314 to the table support frame 24. Joint assembly 322 includes an adjustable rotary locking and unlocking device of the type disclosed in U.S. Pat. No. 5,689,999 to Wiley et al., dated Nov. 25, 1997, the disclosure of which is expressly incorporated herein by reference.

The joint assembly 322 further includes a cylinder having one end attached to joint assembly 322 and the other end attached to elongated spar section 316. Cylinder 326 allows elongated spar section 316 to pivot downward and upward, i.e., decline and incline, relative to the axis of the proximal section 314 and to be locked at a declination angle, or inclination angle relative to the proximal section 314 of the leg support. In other words, elongated spar section 316 can generally be pivoted downward or upward from a plane generally parallel to the plane defined by the patient support 20. Once pivoted downward or upward to a specific angle, elongated spar section 316 can pivot about the joint axis between the proximal section 314 and the elongated spar section 316 and be locked into a number of positions relative to the vertical axis connecting elongated spar section 316 to proximal section 314. The free end of elongated spar section 316 includes a handle 328 and a release lever 332 that controls release and locking of cylinder 326 to control the position of elongated spar section 316.

Figure 11:
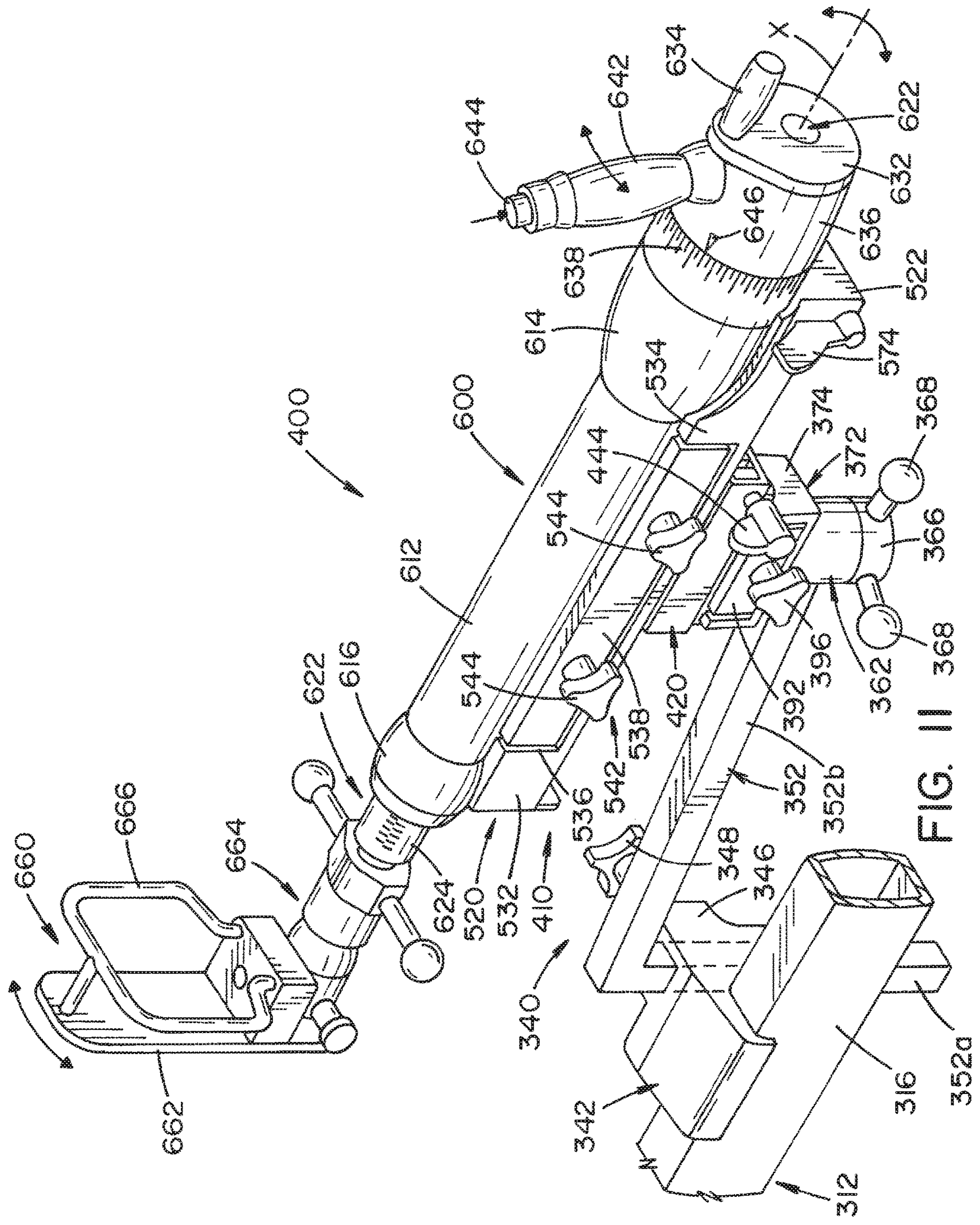
FIG. 11 is a partially-sectioned, perspective view of a traction assembly comprised of a traction device mounted to a slide assembly formed of a support that is movable in a base, the traction assembly shown attached to a mount on a spar section of the orthopedic table.
Figure 12:
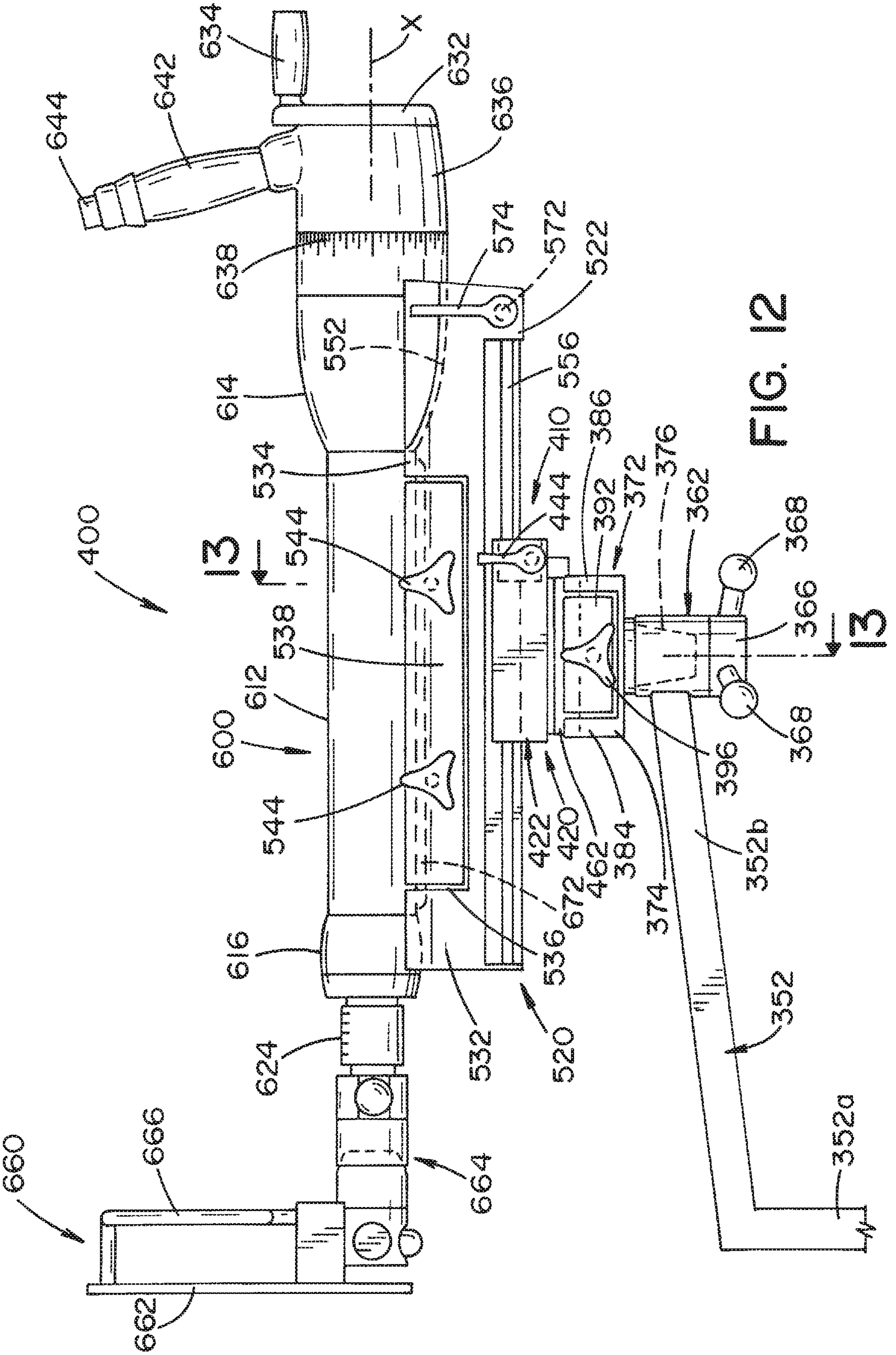
FIG. 12 is a side, elevational view of the traction assembly shown in FIG. 11.

Referring now to FIG. 11, a traction assembly 400 and a mounting structure 340 for attaching traction assembly 400 to elongated spar section 316 are best seen. Mounting structure 340 is comprised of a releasable clamp 342 attachable to spar section 316 of leg support 312, a support arm 352 mounted to clamp 342, and a support hub 362 attached to support arm 352.

Releasable clamp 342 is provided for attachment to elongated spar section 316. Clamp 342 is essentially a C-shaped collar having a first collar adjustment screw 344 (best seen in FIGS. 1 and 2) extending through clamp 342 to lock clamp 342 onto elongated spar section 312. First collar adjustment screw 344 includes a handle and allows for releasably locking of clamp 342 onto elongated spar section 316 at different locations along the length thereof. Clamp 342 includes a mounting boss 346 (best seen in FIG. 11) having an opening extending therethrough. The opening is dimensioned to receive one leg of a generally L-shaped support arm 352. Support arm 352 has a first leg **352*a* and a second leg 352*b*. A second collar adjusting screw 348 having a knob thereon is provided to allow leg 352*a* of support arm 352 to be locked in place relative to clamp 342 at different locations along leg 352*a* of support arm 352. Leg 352*b* of support arm 352 includes a support assembly at the end thereof. The support assembly is comprised of a support hub 362 and a support mount 372. Support hub 362 is generally cylindrical in shape and includes a conical bore 364 (best seen in FIG. 13) formed in one end thereof. Support hub 362 and conical bore 364 are symmetrical about a central axis. Support hub 362 is attached to support arm 352 such that the axis of support hub 362 is generally vertically oriented. A locking wheel 366 has a plurality of radially extending handles 368. Locking wheel 366 includes a threaded shaft 370 that is dimensioned to extend through a hole 369 in the bottom of support hub 362 into conical bore 364**.

Figure 14:
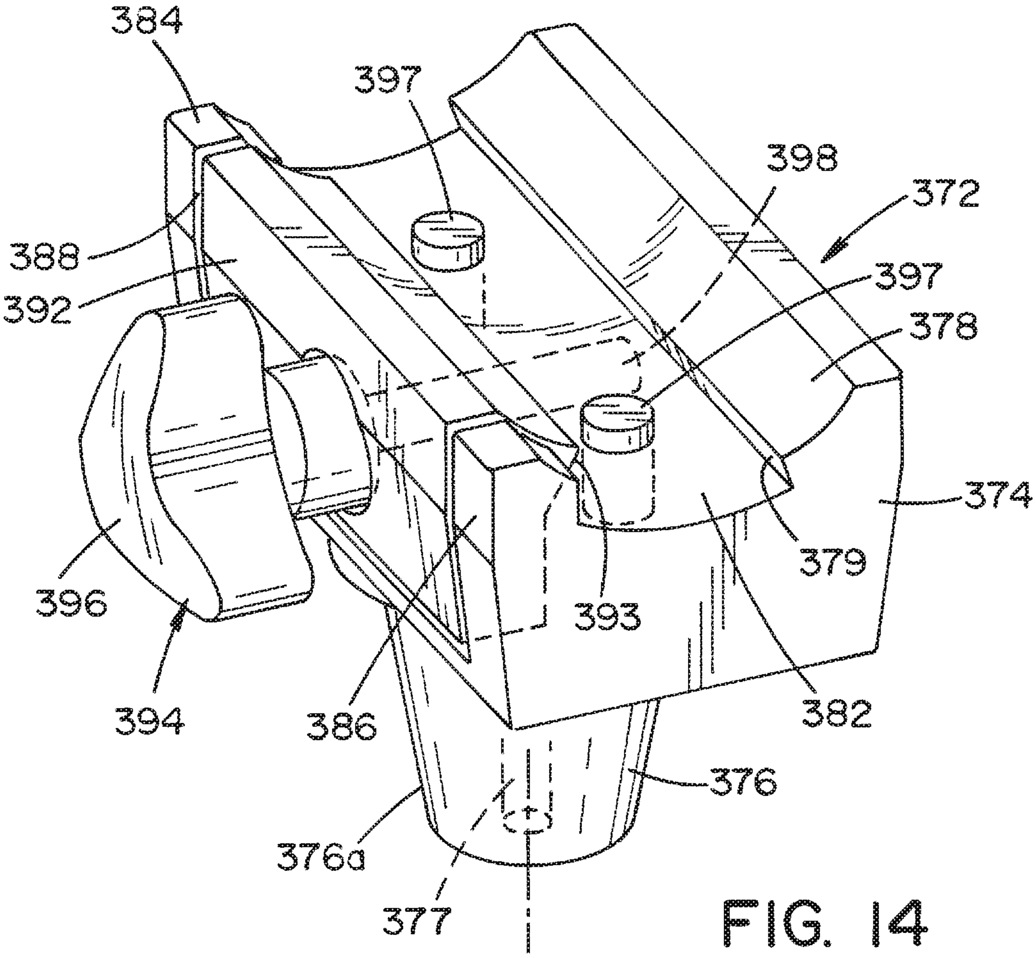
FIG. 14 is a perspective view of a mount used to attach a traction assembly to a leg support of the orthopedic table.

A support mount 372, best seen in FIG. 14, is provided for attachment to support hub 362. Support mount 372 is generally comprised of a body portion 374 and a taper portion 376. Body portion 374 has a first side wall 378 formed along one side thereof. A central channel 382 is formed along the length of body portion 374. Two spaced-apart wall sections 384, 386 are formed along the opposite side of body portion 374. Wall sections 384, 386 define an opening 388 that communicates with channel 382 formed in body portion 374. A movable jaw 392 is dimensioned to be disposed within opening 388 defined between wall sections 384, 386. Jaw 392 is movable relative to channel 382 and opposing side wall 378.

A manually-operable, adjusting device 394 is provided to move jaw 392 relative to channel 382. Adjusting device 394 is comprised of a hand knob 396 having a threaded shaft 398 (best seen in FIG. 13) extending therefrom. Threaded shaft 398 is dimensioned to be screwed into a mating, threaded opening 399 formed in one side of body portion 374 of support mount 372. Rotation of handle knob 396 in a first direction about the longitudinal axis of threaded shaft 398 causes jaw 392 to move toward channel 382. Rotation of handle knob 396 in an opposite direction about the longitudinal axis of threaded shaft 398 causes jaw 392 to move away from channel 382.

The inner face of side wall 378 and the inner face of jaw 392 are undercut to define recessed portions 379, 393, respectively, wherein channel 382 defined by jaw 392 and side wall 378 have generally dove-tail-shapes in cross-section. A plurality of spaced-apart, axially aligned positioning pins 397 extends upward from the lower surface of channel 382. Positioning pins are aligned along the length of channel 382.

Figure 13:
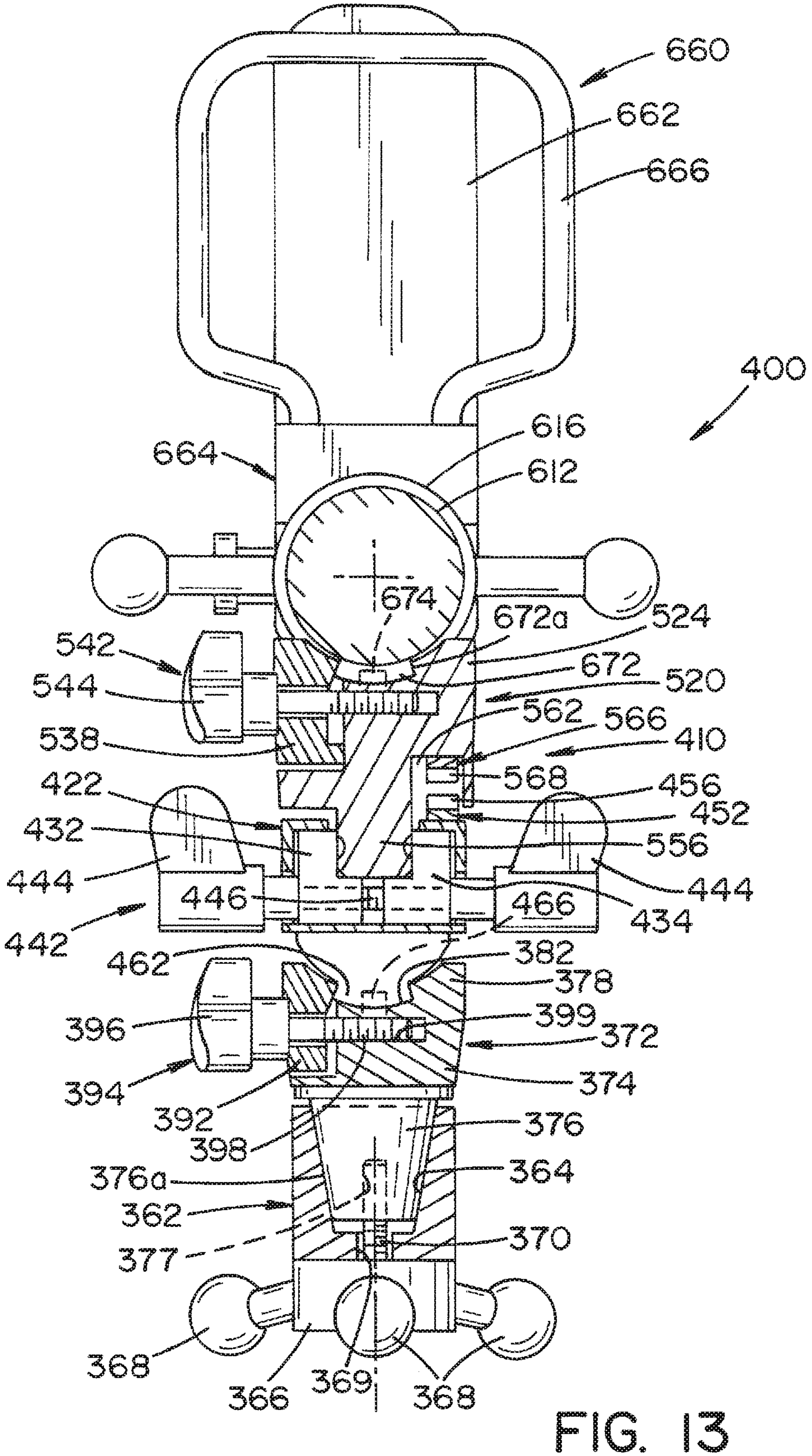
FIG. 13 is a cross-sectional view taken along lines 13-13 of FIG. 12.

Taper portion 376 of support mount 372 is dimensioned to have a conical outer surface **376*a* that conforms and mates with conical bore 364 in support hub 362. As best seen in FIG. 13, threaded shaft 370 on locking wheel 366 is dimensioned to extend into a threaded opening 377 formed in the bottom of taper portion 376. Rotation of locking wheel 366 in one direction is operable to draw taper portion 376 on support mount 372 down into conical bore 364 and into mating engagement with support hub 362 to lock support mount 372 to support hub 362. In this respect, support mount 372 is lockable in any angular position about the axis of support hub 362**.

Figure 15:
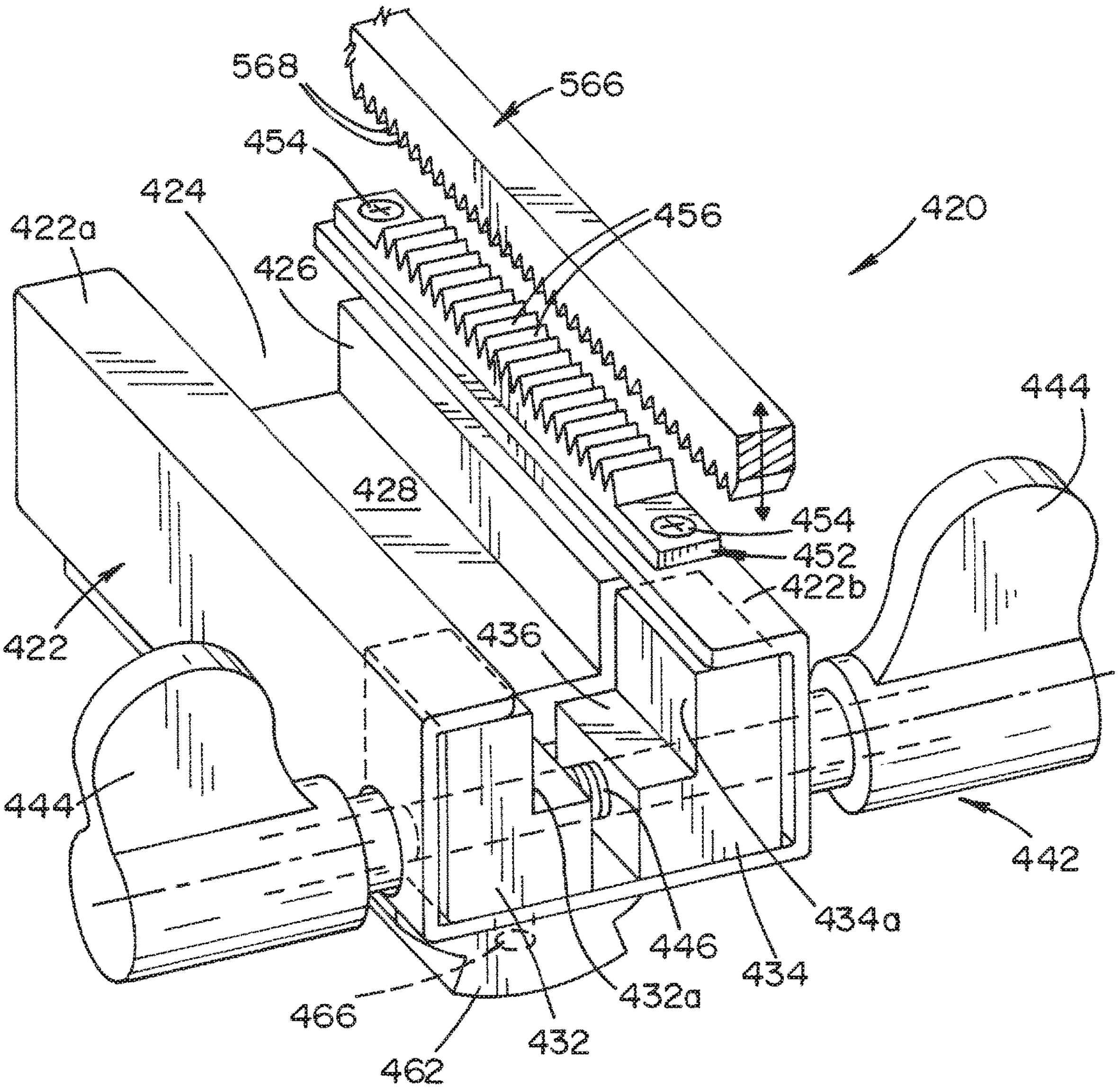
FIG. 15 is a perspective view of a base that forms part of the slide assembly of the traction assembly.

As described above, support mount 372 is dimensioned to receive traction assembly 400 thereon. Traction assembly 400 is comprised of a slide assembly 410 and traction device 600. The slide assembly 410 is basically comprised of a rectangular base 420 and an elongated traction support 520 that is operable to reciprocally slide along base 420. Base 420, best seen in FIG. 15, is comprised of a generally rectangular housing 422 having an elongated opening 424 formed through the upper surface thereof. A pair of flanges **422*a*, 422*b* are formed on the upper surface of housing 422 on opposite sides of opening 424. Housing 422 is preferably formed of extruded metal. A U-shaped block 426 and two spaced-apart plates 432, 434 are disposed within housing 422. U-shaped block 426 defines an elongated slot 428 therethrough. Slot 428 is aligned and in registry with opening 424 in housing 422. Plates 432, 434 define opposing planar faces 432*a*, 434*a* respectively. Spaced-apart plates 432, 434 are arranged such that planar faces 432*a*, 434*a* define a gap 436 of generally rectangular cross-section therebetween. Gap 436 formed between faces 432***a*, 434*a* of plates 432, 434 is disposed to be aligned and in registry with elongated opening 424 defined in the upper surface of housing 422 and with slot 428 formed in U-shaped block 426.

Adjustment screw 442 extends through housing 422 into and through the two spaced-apart plates 432, 434. Adjustment screw 442 is provided to adjust the spacing between faces 432*a*, 434*a* of plates 432, 434. Adjusting screw 442 is similar to adjusting and locking devices 394 described above. In this respect, adjusting screw 442 is basically comprised of two, spaced-apart tab-handles 444 having an elongated threaded shaft 446 extending therebetween. Threaded shaft 446 is dimensioned to be received within threaded openings formed in plates 432, 434. Rotation of threaded shaft 446 in one direction about its axis causes plates 432, 434 to move toward each other so as to reduce the width of gap 436 defined therewith. Rotation of threaded shaft 446 in an opposite direction increases the dimension of gap 436.

An elongated toothed plate 452 is secured to flange 422*b* of housing 422 by conventional fasteners 454. Plate 452 extends parallel to opening 424 in housing 422 and slot 428 in block 426. Plate 452 has a plurality of equally spaced, like teeth 456 extending upward therefrom. An elongated plate 462 is attached to the bottom of housing 422. Plate 462 is attached by conventional fasteners (not shown). Plate 462 extends lengthwise along the underside of housing 422 and has a cross-sectional shape generally conforming to the cross-sectional dove-tail shaped channel 382 defined in support mount 372. In this respect, plate 462 has tapered side walls that are designed to be captured by side wall 378 and jaw 392 of support mount 372. Spaced-apart holes 466 are formed in plate 462 to be aligned with and to receive the locating pins on support mount 372.

Figure 16:
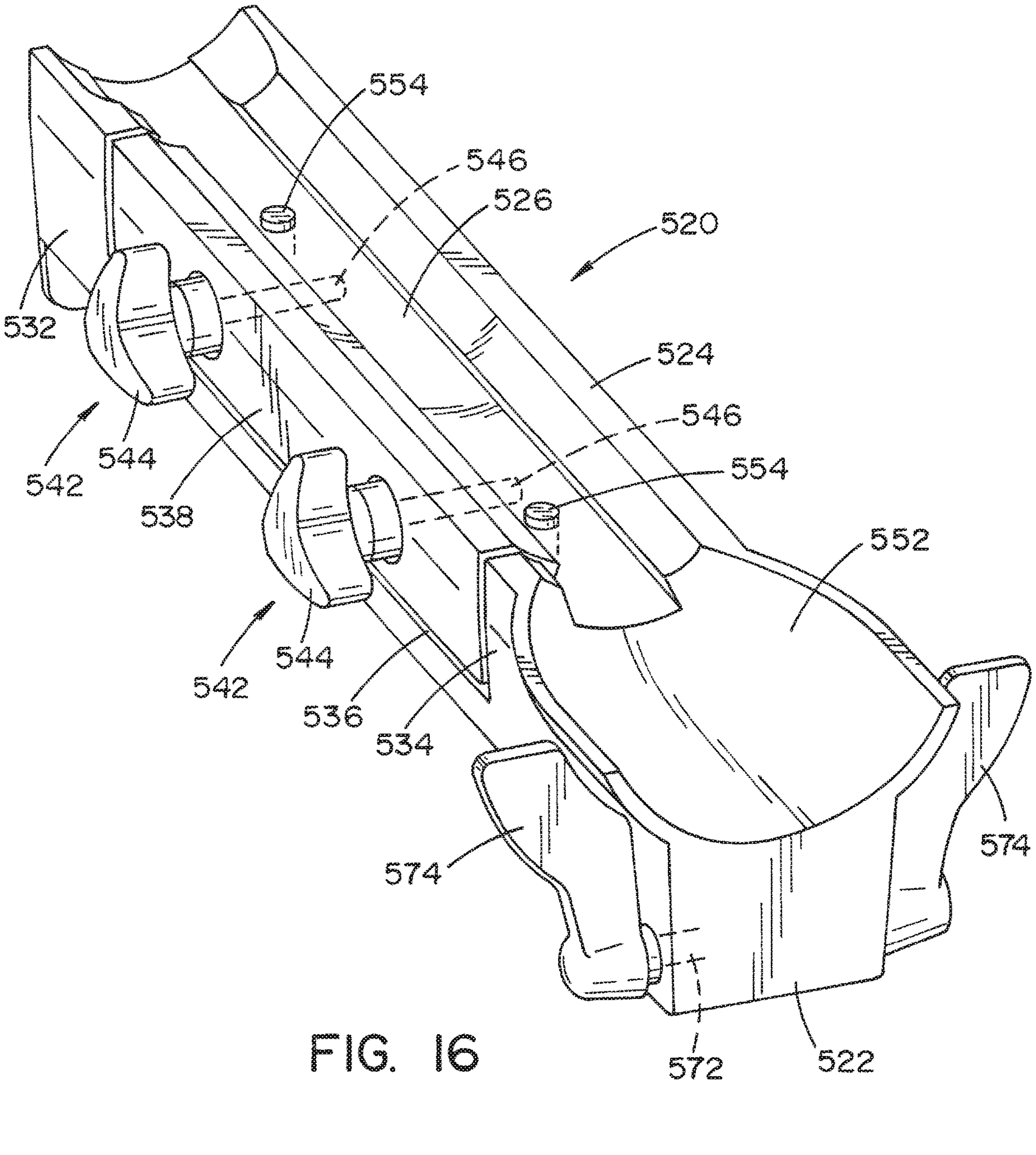
FIG. 16 is a perspective view of a support that forms part of the slide assembly.

Referring now to FIG. 16, elongated traction support 520 is best seen. Elongated traction support 520 is provided to support a traction device 600 and to be reciprocally removable through slot 428 formed in base 420. As shown in the drawings, traction support 520 is significantly longer than base 420. Traction support 520 has an elongated base portion 522 having a side wall 524 formed along the edge of base portion 522. A channel 526 is formed along the length of traction support 520 adjacent side wall 524. Two spaced-apart wall sections 532, 534 are formed along the opposite edge of base portion 522 of traction support 520. Wall sections 532, 534 define an opening 536 that communicates with channel 526. A movable jaw 538 is dimensioned to be disposed in opening 536 defined by wall sections 532, 534. Jaw 538 is movable relative to the opposing side wall 524. Manually operable, adjusting devices 542, similar to adjusting device 394 described above with respect to support mount 372, are operable to move jaw 538 toward and away from opposing side wall 524. Adjusting devices 542 are each comprised of a hand knob 544, similar to those described above, having a threaded shaft 546 extending therefrom. Each threaded shaft 546 is dimensioned to be screwed into a mating, threaded opening formed into the sides of base portion 522. As described above, rotation of knob 544 in one of two directions causes jaw 538 to move toward or away from opposing side wall 524.

As indicated above, channel 526 is formed between side wall 524 on one side of base portion 522 and jaw 538 on the other side of base portion 522. The inner face of side wall 524 and the inner face of jaw 538 are undercut to define notched regions. Together, side wall 524 and jaw 538 define a dove-tail-shaped channel 526 along the length of traction support 520. In accordance with one aspect of the present invention, the dimensions and cross-sectional shape of channel 526 defined along traction support 520 is identical to the dimensions and cross-sectional shape of channel 382 defined in support mount 372. In this respect, jaw 538 on traction support 520 has a similar cross-sectional shape to jaw 392 on support mount 372 with the exception that jaw 538 is longer and includes two adjusting devices 542.

Traction support 520 is formed to have a cup-shaped cavity 552 disposed at one end thereof. Cavity 552 is disposed on the upper surface of traction support 520 and communicates with channel 526 extending along the upper surface of traction support 520. Cavity 552 is dimensioned to accommodate a portion of traction device 600, as shall be described in greater detail below. Locating pins 554 are disposed within channel 526 and extend upward from the surface of base portion 522. Locating pins 554 are aligned along the length of channel 526.

Traction support 520 also includes a bottom rail 556, best seen in FIG. 13, extending along the length and underside thereof. Bottom rail 556 extends along the length of traction support 520 and is generally rectangular in cross-section, and is dimensioned to be received in slot 428 in base 420. Bottom rail 556 is operable to be received within slot 428 and to be reciprocally movable therethrough when adjusting screw 442 in base 420 is positioned to define a clearance between the sides of rail 556 and opposing faces 432*a*, 434*a* of plates 432, 434 within base 420. Rail 556 is operable to be locked into a specific position relative to base 420 by means of adjusting screw 442 described above. In this respect, traction support 520 may be fixed relative to base 420 through adjustment of adjusting screw 442 to cause plates 432, 434 to clap against the sides of bottom rail 556.

A channel 562, best seen in FIG. 13, is formed in the underside of traction support 520 to one side of bottom rail 556. Channel 562 extends along the length of traction support 520 parallel to rail 556. An elongated rack 566, best seen in FIG. 15 and in cross-section in FIG. 13, having spaced-apart, downward-facing teeth 568 dimensioned to mesh with teeth 456 on plate 452 on base 420, is mounted within channel 562. Rack 566 is mounted to be reciprocally movable between a first, lowered position, wherein rack 566 engages and meshes with plate 452 on base 420, and a second, retracted position, wherein rack 566 is spaced from plate 452. Rack 566 is connected to a mechanical linkage (not shown) that in turn is connected to a shaft 572 extending through base portion 522 of traction support 520. Rotation of shaft 572 controls movement of rack 566 between the first, lowered position and the second, retracted position. Shaft 572 is disposed near one end of traction support 520. Lever handles 574 are provided at each end of shaft 572 to allow a member of a surgical team to control movement of rack 566. Rack 566 on traction support 520 and plate 452 on base 420 provide a second mechanism for locking or unlocking traction support 520 to base 420 and provide a means of control, i.e., lever handles 574, near the operative end of traction support 520.

Referring now to FIG. 11, traction device 600 is best seen. Traction device 600 is generally cylindrical in shape and has an outer tubular body 612 having a flared, cup-shaped first end 614. An elongated shaft assembly 622 is dimensioned to extend through tubular body 612 and to have a projecting portion 624 that extends or projects from a second end 616 of tubular body 612. Shaft assembly 622 includes a linear screw mechanism (not shown) disposed within tubular body 612 that allows the length of shaft assembly 622 to increase or decrease along an axis X of shaft assembly 622 based upon rotation of a first end of shaft assembly 622. In the embodiment shown, the length of projecting portion 624 of shaft assembly 622 increases or decreases based upon rotation of the first end of shaft assembly 622. A cap 632 having a crank handle 634 is attached to the first end of shaft assembly 622. Using the crank handle 634, cap 632 and the first end of shaft assembly 622 can be rotated in both directions as illustrated by arrows in FIG. 11. In this respect, turning crank handle 634 in one direction causes shaft assembly 622 to telescope into tubular body 612 of traction device 600. Rotation of crank handle 634 in the opposite direction causes shaft assembly 622 of traction device 600 to move outwardly in small, precise increments from tubular body 612 of traction device 600.

A generally cylindrical collar 636 is disposed between end cap 632 and flared, cup-shaped first end 614 of tubular body 612. Collar 636 is dimensioned such that the outer surface of collar 636 is an extension of the surface of flared, cup-shaped first end 614 of tubular body 612. Collar 636 includes a grip handle 642 oriented generally perpendicular to axis X of traction device 600. A release button 644 is provided on the free end of handle 642. Release button 644 is connected to a locking mechanism (not shown) within tubular body 612 that locks shaft assembly 622 to tubular body 612 so as to prevent angular rotation of shaft assembly 622 about axis X. Depression of release button 644 releases the locking mechanism and allows shaft assembly 622 to rotate angularly about axis X. As best seen in FIG. 11, a scale 638 is provided along the end surface of the flared, cup-shaped first end 614 of tubular body 612. A marker indicator 646 on collar 636 is disposed opposite to scale 638 to provide an indication of the amount of angular rotation of shaft assembly 622. Release of release button 644 on grip handle 642 will lock shaft assembly 622 in the position of shaft assembly 622 at the time release button 644 is released.

A boot support 660 is attached to the free end of shaft assembly 622. As will be described in greater detail below, boot support 660 is provided to attach to a boot (not shown) on a patient's foot during a surgical procedure. Boot support 660 is basically comprised of a flat plate 662 secured to a mounting assembly 664 on the free end of shaft assembly 622. Plate 662 is operable to move with shaft assembly 622 either linearly along axis X or rotationally about axis X. In the embodiment shown, a handrail or handgrip 666 is provided on the back side of plate 662, nearer to traction device 600.

Figure 17:
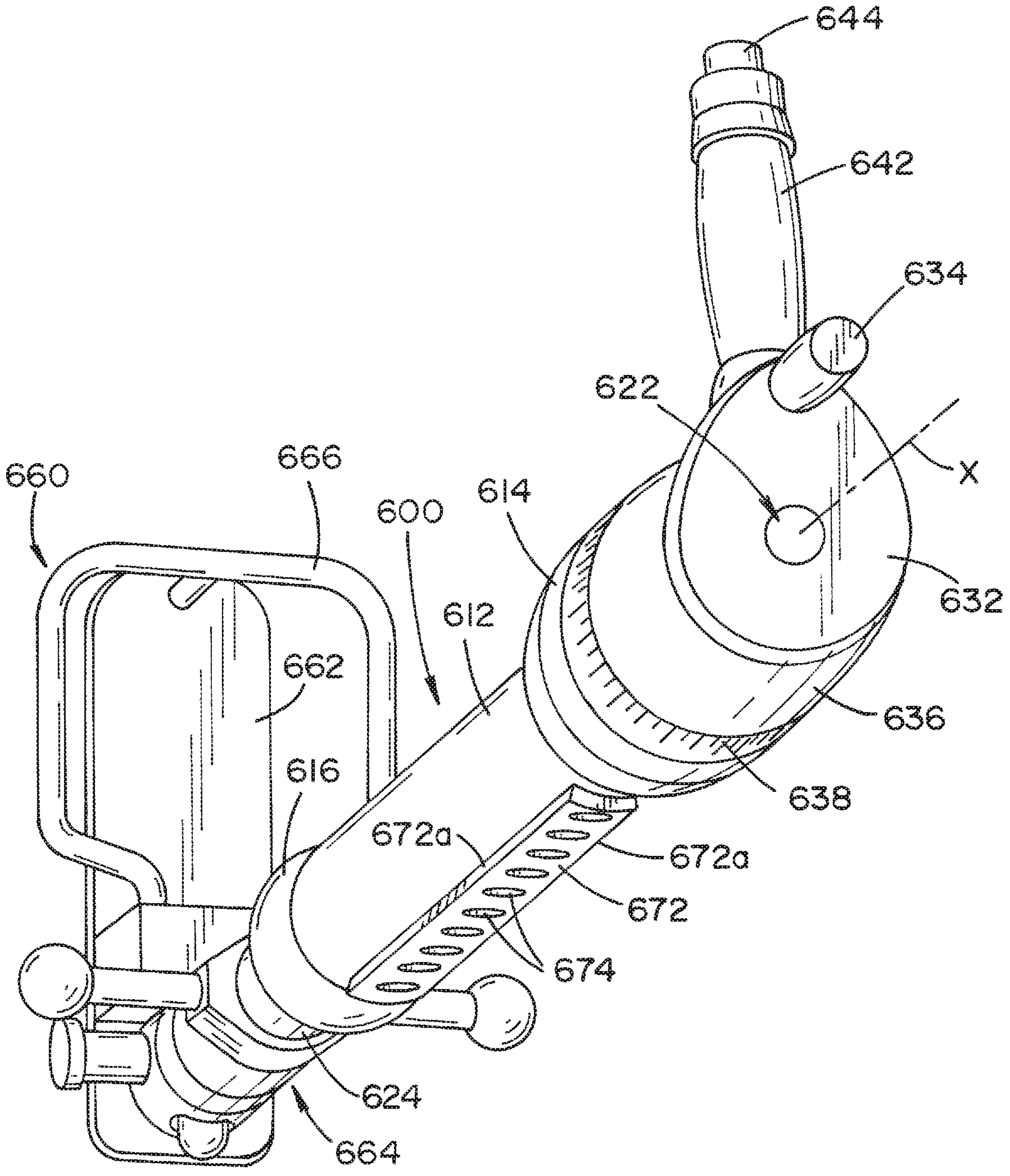
FIG. 17 is a perspective view of a traction device that is mounted to the slide assembly to form the traction assembly.

An elongated plate 672 extends along the underside of tubular body 612, as best seen in FIG. 17. Plate 672 is attached to tubular body 612 by conventional fasteners (not shown). A plurality of spaced-apart apertures 674 are aligned along plate 672. Apertures 674 are dimensioned and spaced to allow traction device 600 to be mounted onto pins 554 at different locations along traction support 520. In addition, apertures 674 are dimensioned and spaced to allow traction device 600 to be mounted on pins 397 of support mount 372. The lateral edge or sides 672*a* of plate 672 are undercut and slope inward to be matingly received in notched regions 382, 526 on support mount 372 and traction support 520. Once traction device 600 is set in place in a desired position along traction support 520, traction device 600 may be locked in place thereon by adjusting the position of jaw 538 inward to capture plate 672. In a similar manner, traction device 600 may be mounted to support mount 372 by adjusting the position jaw 392.

Referring now to the operation of the orthopedic table 10, orthopedic table 10 is primarily designed for surgical procedures involving a patient's legs and more specifically, to surgical procedures such as knee replacement, pinning of leg bones, or total hip replacements.

Figure 3:
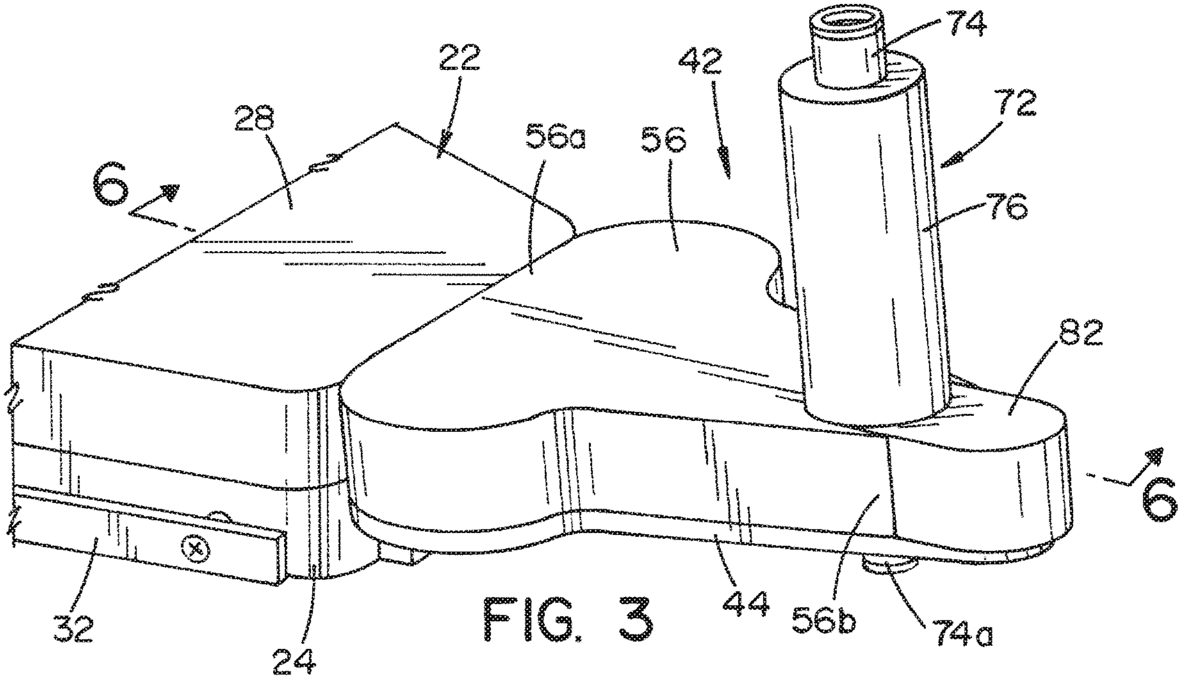
FIG. 3 is a perspective view of a sacral pad assembly comprised of a sacral pad and a post pad, the sacral pad assembly forming part of a patient support of the orthopedic table shown in FIG. 1.
Figure 5:
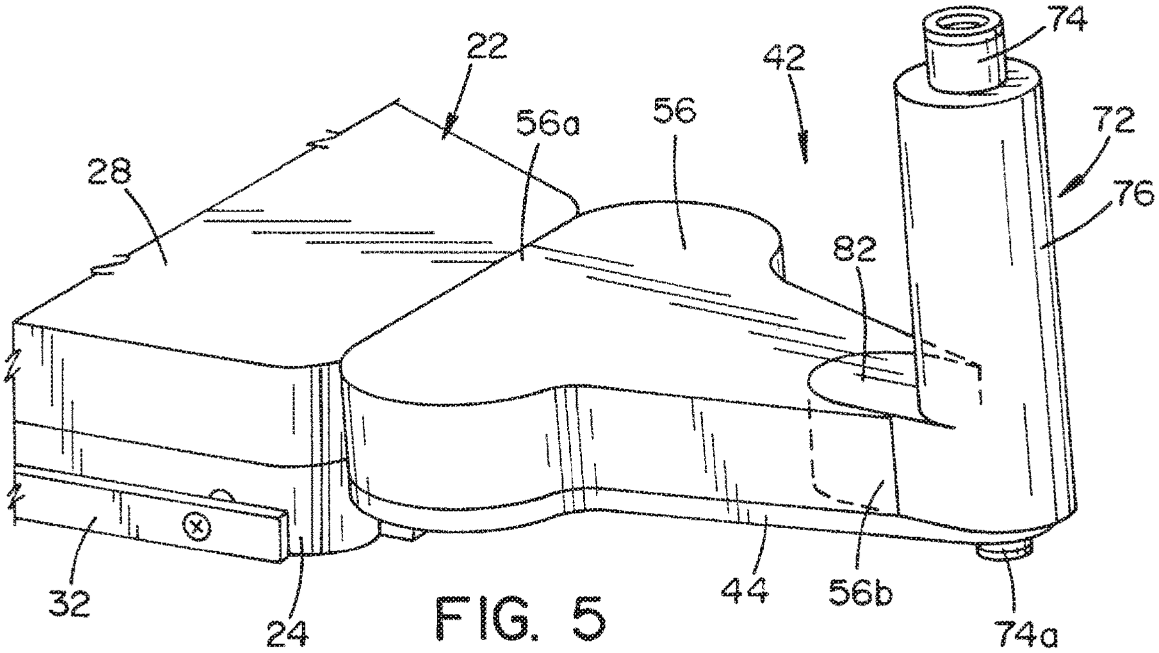
FIG. 5 is a perspective view of the sacral pad assembly shown in FIG. 3, showing the post pad disposed in a second position relative to the sacral pad.

Prior to any of the foregoing surgical procedures, a patient is positioned, face up, on the patient support 20. The patient's head and torso are supported by head/torso support 22. The patient's hips are supported by sacral support 42 with the patient's crotch positioned against the vertical, positioning post 72 on the sacral support 42. In accordance with one aspect of the present invention, depending upon the height, i.e., length, of the patient, the positioning post 72 may be positioned in one of the two positions on the sacral plate 44, as illustrated in FIGS. 3 and 5.

With a patient lying on patient support 20 with the patient's legs positioned over leg supports 312A, 312B, each of the patient's feet are secured within boots (not shown) that are attached to plate 662 on boot support 660 of traction device 600. If necessary, the position of traction device 600 relative to the patient may be adjusted in several ways. For example, clamp 342 may be repositioned along elongated spar section 316 through use of first collar adjusting screw 344. Support arm 352 may be adjusted relative to clamp 342 by means of second collar adjusting screw 348. Similarly, the angular position of support mount 372 relative to the axis of support hub 362 may be modified using locking wheel 366. Still further, traction support 520 having traction device 600 thereon may be moved relative to base 420 using either adjusting screw 442 on base 420 or lever handles 574 on traction support 520. In this respect, loosening the adjusting screw on the base and/or disengaging the rack on the support from the plate on the base, allows the support to freely slide relative to the base.

During hip replacement surgery, an incision is made into the patient's hip. The leg muscles are then separated to allow access to the hip. The femur ball is then cut from the femur while the ball is still in the hip socket. The femur ball is then removed from the hip socket. Once the femur is separated from the hip, the cartilage in the hip socket or acetabulum is then removed by the surgeon. An acetabular implant component or cup is then inserted in the surgically modified hip, typically by cement, special screws or mesh that accepts bone growth to firmly affix the cup to the pelvis.

At a certain stage in the procedure, the femur hook 182, which at this time is separate from the femur support assembly 112, is inserted into the patient's leg to capture the femur bone of the patient. The end of the femur is removed from the patient's leg using the femur hook 182. The femur hook 182 with the femur thereon is then mounted to hook support 162 by inserting post 184 at the lower end of femur hook 182 into one of the plurality of apertures 172 on hook support 162. As illustrated in FIGS. 7 and 8, femur hook 182 may be oriented in any one of several positions in a specific aperture 172 in hook support 162. As indicated above, hook support 162 includes a plurality of aligned apertures 172, each defining a location where femur hook 182 may be inserted. Thus, the physician may choose a most convenient location and one of different angular positions at that location. The ability of hook support 162 to pivot about pin portion 156, as illustrated in FIG. 7, facilitates positioning of femur hook 182 in a suitable aperture 172 on hook support 162.

During the procedure, the height, i.e., the elevation, of the femur bone may be adjusted using the femur support assembly 112. In this respect, a gross adjustment to the height of femur hook 182 on hook support 162 may be made using spring-biased locking pin 148 and bores 146 in elongated rod 144. In this respect, the physician may choose one of several elevated positions by merely removing spring-biased locking pin 148 from its locked position relative to rod 144 and elevate rod 144 to a desired position and reinsert locking pin 148. Further vertical adjustments of hook support 162 and femur hook 182 may be made by initiating the powered lifting device 128 in one direction or another to provide fine adjustment of the height of the end of the femur.

The elongated spar section 316 of leg support 312A is released to allow the elongated spar section 316 to pivot downwardly from a horizontal position to a declined position. Prior to pivoting spar section 316 downward, adjusting screw 442 on base 420 of slide assembly 410 is "released" to allow the traction support 520 to move freely relative to base 420. In this respect, with the patient's foot secured to plate 662 on traction device 600, when elongated spar section 316 is pivoted downward, traction device 600 is allowed to move with the patient's foot as spar section 316 moves downward. Typically, because of the attachment to the patient's foot and leg, as spar section 316 pivots downward, traction device 600 and traction support 520 will move relative to base 420. In this respect, if traction device 600 is locked relative to base 420, the patient's leg would basically be stretched as elongated spar section 316 is pivoted downwardly. By providing a slide assembly 410 that allows traction support 520 to slide relative to base 420, elongated spar section 316 may pivot freely downward without placing undue tension or stress on the patient's leg.

Once elongated spar section 316 is in a desired declined position, traction support 520 holding traction device 600 may be locked relative to base 420 by use of adjustment screw 442. Traction device 600 is basically locked into position relative to elongated spar section 316 of leg support 312A. Further, minor axial adjustment of the leg along elongated spar section 316 may be made using crank handle 634 on traction device 600. Crank handle 634 basically allows the leg to be stretched or pushed in small increments along an axis that is essentially parallel to elongated spar section 316.

With the femur removed from the patient's hip, the patient's leg may also be pivoted to one side or another about axis X of traction device 600 using grip handle 642 on traction device 600. In this respect, by depressing release button 644 on grip handle 642, the locking mechanism (not shown) within traction device 600 allows shaft assembly 622 (and foot support 660) to be rotated angularly from side-to-side relative to axis X. In other words, a patient's foot, and therefore his entire leg, can be rotated to either side along axis X of traction device 600. (Because the ball is not connected to the hip socket, the leg can easily rotate about axis X of traction device 600).

With the femur supported on femur hook 182 at a desired location and elevation, traction device 600 may be used to make minor adjustments lengthwise with respect to the position of the femur. Once in a desired position, the surgeon may proceed with the surgery by reaming the femoral canal and attaching a metal ball to the stem to act as a hip pivot point within the cup.

Upon completion of the necessary surgical steps, traction support 520 of slide assembly 410 is released from base 420 by reversing the rotation of adjusting screws 442. The elongated spar section 316 is then pivoted back to a horizontal position relative to the patient's torso. The patient's femur may then be rotated back to its normal position relative to the patient's hip using grip handle 642 and release button 644 thereon. In this respect, graduated scale 638 on collar 636 of traction device 600 may be used to insure that the femur is returned to its original position relative to the patient's repaired hip socket.

The ability to rapidly reposition the patient's leg during the declining and inclining of elongated spar section 316 during the procedure, significantly reduces the duration of the surgical procedure. In this respect, slide assembly 410, when in a released configuration, allows traction device 600 to slide reciprocally relative to base 420 and relative to elongated spar section 316 during the vertical movement thereof. Once in a desired position, traction support 520 and base 420 of slide assembly 410 may be locked relative to each other and further fine adjustments made by crank handle 634 on traction device 600.

Figure 18:
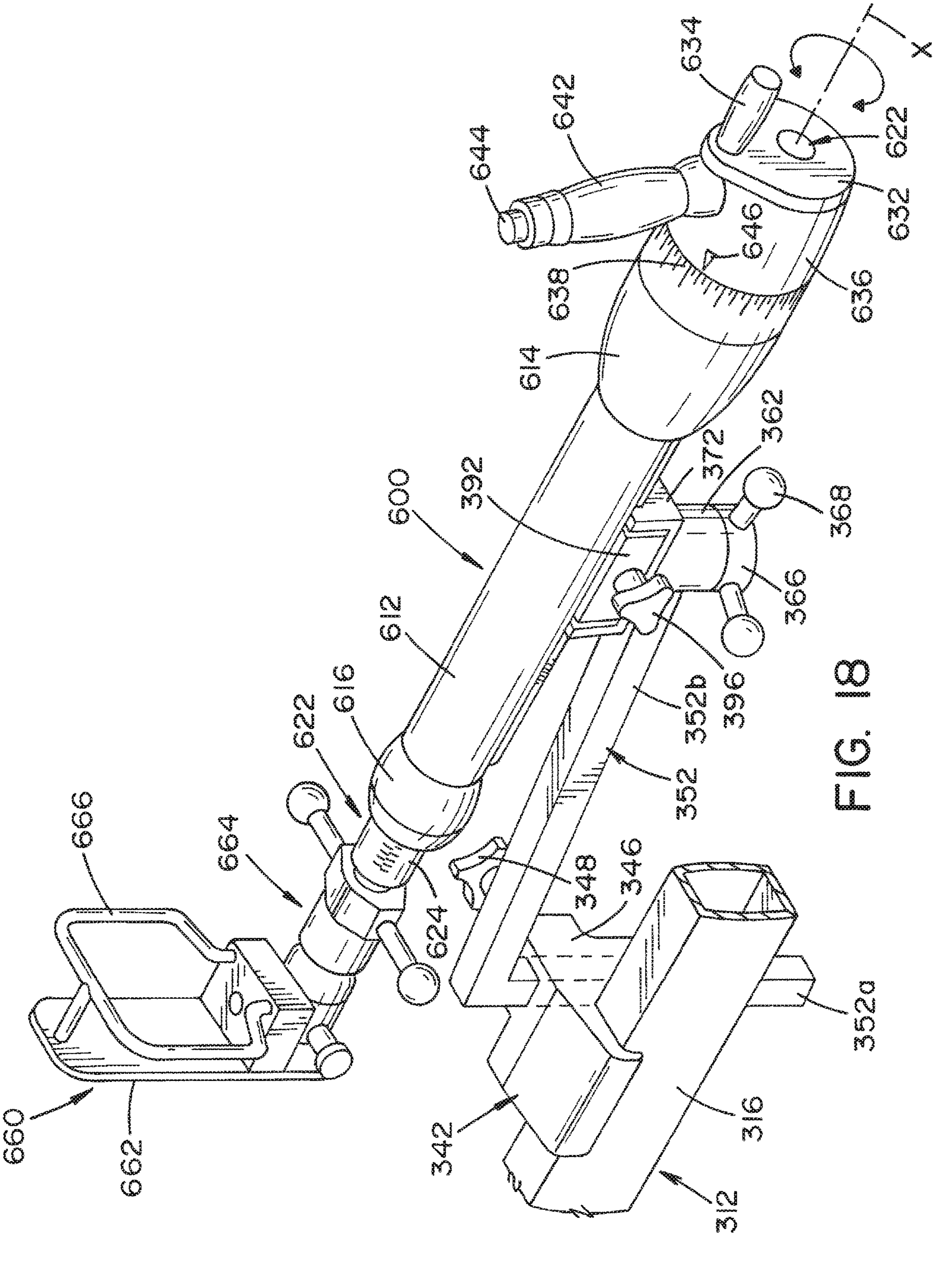
FIG. 18 is a perspective view of a traction device, with a slide assembly, mounted to a spar section of the leg support of the orthopedic table.

While slide assembly 410 is particularly useful and applicable with respect to a total hip arthroplasty (THA), such a structure may not be required in a conventional knee surgery or a surgical procedure for applying pins to certain leg bones. In these procedures, lengthwise elongation or contraction of the leg may be required. According to the present invention, the slide assembly 410 discussed above, specifically traction support 520 and base 420, may be removed from orthopedic table 10 and traction device 600 may be mounted directly to support mount 372, as illustrated in FIG. 18. In this respect, because the leg typically remains in a horizontal orientation during knee surgery, gross adjustment of the boot support assembly is not required. Thus, for orthopedic tables that are not used in total hip replacements, traction device 600 is mounted directly to support mount 372 on elongated spar section 316.

The foregoing description is a specific embodiment of the present invention. It should be appreciated that this embodiment is described for purposes of illustration only, and that numerous alterations and modifications may be practiced by those skilled in the art without departing from the spirit and scope of the invention. It is intended that all such modifications and alterations be included insofar as they come within the scope of the invention as claimed or the equivalents thereof.

Having described the invention, the following is claimed:

1. A patient support apparatus, comprising:

an upper body support configured to support a head and torso section and a sacral section of the patient;

a leg support configured to support a leg of the patient, the leg support being attached to the upper body support, the leg support comprising:

a proximal leg support section having a first end and a second end, the first end of the proximal leg support section being connected to the upper body support, the proximal leg support section being configured to rotate at the upper body support about a first vertical axis relative to the upper body support;

a joint assembly connected to the second end of the proximal leg support section;

an elongated spar support section having a first end and a second end, the first end of the elongated spar support section being connected to the second end of the proximal leg support section by the joint assembly, the joint assembly being configured to enable rotation of the elongated spar support section about a second vertical axis relative to the proximal leg support section and pivoting of the elongated spar support section about a horizontal axis relative to the proximal leg support section; and a handle assembly positioned at the second end of the elongated spar support section, the handle assembly being configured to control the enabled rotation and pivoting of the elongated spar support section;

a mounting structure releasably attached to the elongated spar support section; and a traction assembly removably attached to the elongated spar support section via the mounting structure, the traction assembly comprising:

a traction assembly body having a first end and a second end;

a traction assembly shaft assembly dimensioned to telescopically extend through the traction assembly body, the traction assembly shaft assembly having a traction assembly shaft body portion disposed within the traction assembly body and a traction assembly projecting portion that projects from the second end of the traction assembly body;

a traction assembly boot support attached to the traction assembly projecting portion of the traction assembly shaft assembly, the traction assembly shaft body portion of the traction assembly shaft assembly being rotatable about an axis of the traction assembly shaft assembly to adjust a length of the traction assembly projecting portion and a linear position of the traction assembly boot support; and a traction assembly collar disposed at the first end of the traction assembly body and dimensioned to be an extension of the first end of the traction assembly body, the traction assembly collar being connected to the traction assembly shaft body portion of the traction assembly shaft assembly, the traction assembly collar being rotatable about the axis of the traction assembly shaft assembly to rotate the traction assembly shaft assembly to adjust an angular position of the traction assembly boot support.

2. The apparatus of claim 1, wherein the leg support further comprises a cylinder having a first end and a second end, the first end of the cylinder being connected to a portion of the joint assembly, the second end of the cylinder being connected to the elongated spar support section, the cylinder being configured to allow the pivoting of the elongated spar support section enabled by the joint assembly.

3. The apparatus of claim 2, wherein the handle assembly comprises a release lever, the release lever being operable to control an ability of the cylinder to allow the pivoting of the elongated spar support section.

4. The apparatus of claim 3, wherein the release lever is configured to control release and locking of the cylinder, and wherein the release and locking of the cylinder corresponds with the ability of the cylinder to allow the pivoting of the elongated spar support section.

5. The apparatus of claim 1, wherein the handle assembly comprises a handle, the handle being configured to control positioning of the elongated spar support section such that the elongate spar support section is lockable into a plurality of positions relative to the second vertical axis.

6. A patient support apparatus, comprising:

an upper body support configured to support a head and torso section and a sacral section of the patient;

a leg support configured to support a leg of the patient, the leg support being attached to the upper body support, the leg support comprising:

a proximal leg support section having a first end and a second end, the first end of the proximal leg support section being connected to the upper body support, the proximal leg support section being configured to rotate at the upper body support about a first vertical axis relative to the upper body support;

an elongated spar support section having a first end and a second end; and a joint assembly connecting the first end of the elongated spar support section to the second end of the proximal leg support section, the joint assembly being configured to allow the elongated spar support section to rotate about a second vertical axis relative to the proximal leg support section and pivot about a horizontal axis relative to the proximal leg support section;

a mounting structure releasably attached to the elongated spar support section; and a traction device mounted directly to the mounting structure, the traction device comprising:

a traction device body having a first end and a second end;

a traction device shaft assembly dimensioned to telescopically extend through the traction device body, the traction device shaft assembly having a traction device shaft body portion disposed within the traction device body and a traction device projecting portion that projects from the second end of the traction device body;

a traction device boot support attached to the traction device projecting portion of the traction device shaft assembly, the traction device shaft body portion of the traction device shaft assembly being rotatable about an axis of the traction device shaft assembly to adjust a length of the traction device projecting portion and a linear position of the traction device boot support; and a traction device collar disposed at the first end of the traction device body and dimensioned to be an extension of the first end of the traction device body, the traction device collar being connected to the traction device shaft body portion of the traction device shaft assembly, the traction device collar being rotatable about the axis of the traction device shaft assembly to rotate the traction device shaft assembly to adjust an angular position of the traction device boot support.

7. A patient support apparatus, comprising:

an upper body support configured to support a head and torso section and a sacral section of the patient;

a leg support configured to support a leg of the patient, the leg support being attached to the upper body support, the leg support comprising:

a proximal leg support section having a first end and a second end, the first end of the proximal leg support section being connected to the upper body support, the proximal leg support section being configured to rotate at the upper body support about a first vertical axis relative to the upper body support;

an elongated spar support section having a first end and a second end; and a joint assembly connecting the first end of the elongated spar support section to the second end of the proximal leg support section, the joint assembly being configured to allow the elongated spar support section to rotate about a second vertical axis relative to the proximal leg support section and pivot about a horizontal axis relative to the proximal leg support section;

a mounting structure releasably attached to the elongated spar support section; and a traction assembly that is removably secured to the elongated spar support section via the mounting structure, the traction assembly being rotatable about an axis through the mounting structure, the traction assembly being lockable in a fixed position relative to the mounting structure and the elongated spar support section, the traction assembly being configured to follow movement of a foot of the patient during movement of the elongated spar support section when said traction assembly is unlocked from the fixed position relative to the mounting structure, the traction assembly comprising:

a traction assembly boot support positioned at an end of the traction assembly, the boot support being configured to support the foot of the patient, the boot support being further configured to move along the axis extending through the traction assembly, the boot support being further configured to rotate about the axis extending through the traction assembly; and a traction assembly collar positioned at an opposite end of the traction assembly from the traction assembly boot support, the traction assembly collar being rotatable about the axis of the traction assembly to rotate the traction assembly to adjust an angular position of the traction assembly boot support.

8. A patient support apparatus, comprising:

an upper body support having one or more pads configured to support a torso and a hip of the patient in a generally horizontal orientation;

a leg support configured to support a leg of the patient, the leg support being attached to the upper body support, the leg support comprising:

a proximal leg support section having a first end and a second end, the first end of the proximal leg support section being connected to the upper body support, the proximal leg support section being configured to rotate at the upper body support about a first vertical axis relative to the upper body support;

an elongated spar support section having a first end and a second end; and a joint assembly connecting the first end of the elongated spar support section to the second end of the proximal leg support section, the joint assembly being configured to allow the elongated spar support section to rotate about a second vertical axis relative to the proximal leg support section and pivot about a horizontal axis relative to the proximal leg support section;

a mounting structure releasably attached to the elongated spar support section; and a traction device that is removably secured to the elongated spar support section via the mounting structure and a slide assembly, the slide assembly being configured to secure the traction device stationary relative to the elongated spar support section and allow the traction device to slide relative to the elongated spar support section, the traction device being configured to attach a leg of the patient thereto, the traction device bring further configured to exert a traction force on the leg of the patient along an axis of the traction device, the traction device comprising a traction device collar positioned at an opposite end of the traction device from an end of the traction device at which the leg is attached, the traction device collar being rotatable about an axis of the traction device to rotate the traction device to adjust an angular position of the leg.

9. A patient support apparatus, comprising:

an upper body support configured to support a head and torso section and a sacral section of the patient;

a leg support configured to support a leg of the patient, the leg support being attached to the upper body support, the leg support comprising:

a proximal leg support section having a first end and a second end, the first end of the proximal leg support section being connected to the upper body support, the proximal leg support section being configured to rotate at the upper body support about a first vertical axis relative to the upper body support;

an elongated spar support section having a first end and a second end; and a joint assembly connecting the first end of the elongated spar support section to the second end of the proximal leg support section, the joint assembly being configured to allow the elongated spar support section to rotate about a second vertical axis relative to the proximal leg support section and pivot about a horizontal axis relative to the proximal leg support section;

a mounting structure, comprising:

a mounting structure releasable clamp releasably attached to the elongated spar support section, the mounting structure releasable clamp being configured to attach to the elongated spar support section at a plurality of locations along a length of the elongated spar support section;

a mounting structure support arm mounted to the mounting structure releasable clamp; and a mounting structure support hub attached to the mounting structure support arm;

a support mount attached to the mounting structure support hub; and a traction device removably attached to the mounting structure via the support mount, the traction device comprising:

a traction device body having a first end and a second end;

a traction device shaft assembly dimensioned to telescopically extend through the traction device body, the traction device shaft assembly having a traction device shaft body portion disposed within the traction device body and a traction device projecting portion that projects from the second end of the traction device body;

a traction device boot support attached to the projecting portion of the traction device shaft assembly, the traction device shaft body portion of the traction device shaft assembly being rotatable about an axis of the traction device shaft assembly to adjust a length of the traction device projecting portion and a linear position of the traction device boot support; and a traction device collar disposed at the first end of the traction device body and dimensioned to be an extension of the first end of the traction device body, the traction device collar being connected to the traction device shaft body portion of the traction device shaft assembly, the traction device collar being rotatable about the axis of the traction device shaft assembly to rotate the traction device shaft assembly to adjust an angular position of the traction device boot support.

10. The apparatus of claim 9, wherein the mounting structure support arm is comprised of a mounting structure first support arm leg and a mounting structure second support arm leg, the mounting structure first support arm leg being received by an opening of the mounting structure releasable clamp, the mounting structure support hub being mounted on the mounting structure second support arm leg.

11. The apparatus of claim 10, wherein the mounting structure first support arm leg is connected to the mounting structure second support arm leg to define an L-shape of the mounting structure support arm.

12. The apparatus of claim 10, wherein the mounting structure releasable clamp is configured to lock the mounting structure first support arm leg in place in the opening of the mounting structure releasable clamp at a plurality of locations along a length of the mounting structure first support arm leg.

13. The apparatus of claim 10, wherein the mounting structure support hub is attached to an end of the mounting structure second support arm leg such that an axis of the mounting structure support hub is vertically oriented.

14. The apparatus of claim 9, wherein the mounting structure support hub is attached to an end of the mounting structure support arm such that an axis of the mounting structure support hub is vertically oriented, wherein a mounting structure conical bore is formed in one end of the mounting structure support hub, the mounting structure support hub and the mounting structure conical bore being symmetrical about the axis of the mounting structure support hub.

15. The apparatus of claim 14, wherein the support mount has a taper portion that is dimensioned to have a conical outer surface that is configured to conform and mate with the mounting structure conical bore in the mounting structure support hub.

16. The apparatus of claim 15, wherein a locking wheel is attached to an end of the support hub opposite the end in which the conical bore is formed, wherein a threaded shaft extends from the locking wheel through the opposite end of the support hub into the an area surrounded by the conical bore, wherein the support mount has a threaded opening formed in a tapered end of the taper portion, and wherein, the threaded shaft is inserted into the threaded opening, the locking wheel is configured to rotatably draw the taper portion into the conical bore and into mating engagement with the support hub to lock the support mount to the support hub.

17. The apparatus of claim 15, wherein the support mount is rotatable relative to the mounting structure support hub about the axis of the mounting structure support hub through rotation of the taper portion of the support mount in the mounting structure conical bore of the mounting structure support hub.

18. The apparatus of claim 14, wherein the axis of the mounting structure support hub is perpendicular to the axis of the traction device.

19. The apparatus of claim 9, further comprising:

an intermediate slide assembly configured to removably attach the traction device to the mounting structure via the support mount, the intermediate slide assembly comprising:

an intermediate slide assembly traction support configured to support the traction device, the intermediate slide assembly traction support being attachable to the traction device body; and an intermediate slide assembly base on which the traction support is configured to reciprocally slide, the intermediate slide assembly base being mounted on the support mount.

20. The apparatus of claim 9, wherein the traction device shaft body portion of the traction device shaft assembly has a traction device crank attached thereto at the first end of the traction device body, the traction device crank being configured to rotate the traction device shaft body portion of the traction device shaft assembly about the axis of the traction device shaft assembly to adjust the length of the traction device projecting portion and a linear position of the traction device boot support.

21. The apparatus of claim 20, wherein the traction device shaft assembly comprises a traction device cap attached to the traction device shaft body portion of the traction device shaft assembly at the first end of the traction device body, the traction device cap comprising the traction device crank, and wherein the traction device crank is configured to rotate the traction device cap and the traction device shaft body portion of the traction device shaft assembly about the axis of the traction device shaft assembly to adjust the length of the traction device projecting portion and a linear position of the traction device boot support.

22. The apparatus of claim 20, wherein the traction device crank is further configured to move the traction device shaft assembly telescopically within the traction device body.

23. The apparatus of claim 9, wherein the traction device collar comprises a traction device collar handle extending away from the traction device body, the traction device collar handle being configured to rotate the traction device shaft assembly to adjust the angular position of the traction device boot support.

24. The apparatus of claim 23, wherein the traction device collar handle comprises a traction device release button on a free end thereof, the traction device release button being configured to control an ability of the traction device collar handle to rotate the traction device shaft assembly.

25. The apparatus of claim 9, wherein the traction device collar is configured to allow a gross traction of the traction device to be set and a rotation of the traction device boot support while the elongated spar support section is being articulated.

26. The apparatus of claim 25, wherein the second end of the elongated spar support section has a handle, the handle being configured to allow articulation of the elongated spar support section to control rotation of the elongated spar support section about the second vertical axis relative to the proximal leg support section via the joint assembly, the handle being further configured to allow articulation of the elongated spar support section to control pivoting of the elongated spar support section about the horizontal axis relative to the proximal leg support section via the joint assembly.

* * * * *